United States Patent [19]
Chan

[11] Patent Number: 6,120,511
[45] Date of Patent: Sep. 19, 2000

[54] DRILL GUIDE ASSEMBLY AND METHOD FOR PRODUCING A BONE TUNNEL

[76] Inventor: Kwan-Ho Chan, 4803 1st Pl., Lubbock, Tex. 79416

[21] Appl. No.: 08/972,859

[22] Filed: Nov. 18, 1997

[51] Int. Cl.[7] .................................................. A61B 17/17
[52] U.S. Cl. .............................. 606/96; 606/102; 606/80; 606/179
[58] Field of Search ................................. 606/96, 97, 98, 606/86, 81, 80, 179

[56] References Cited

U.S. PATENT DOCUMENTS

| | | |
|---|---|---|
| 4,672,957 | 6/1987 | Hourahane . |
| 4,722,331 | 2/1988 | Fox . |
| 4,739,751 | 4/1988 | Sapega et al. . |
| 4,781,182 | 11/1988 | Purnell et al. . |
| 4,920,958 | 5/1990 | Walt et al. . |
| 5,112,337 | 5/1992 | Paulos et al. . |
| 5,152,764 | 10/1992 | Goble ........................................ 606/96 |
| 5,154,720 | 10/1992 | Trott et al. . |
| 5,163,940 | 11/1992 | Bourque . |
| 5,403,321 | 4/1995 | DiMarco .................................... 606/96 |
| 5,458,602 | 10/1995 | Goble et al. .............................. 606/96 |
| 5,613,971 | 3/1997 | Lower et al. .............................. 606/96 |

OTHER PUBLICATIONS

Boszotta, Harald, M.D., "Arthroscopic Anterior Cruciate Ligament Reconstruction Using A Patellar Tendon Graft in Press–Fit Technique: Surgical Technique and Follow–up", Arthroscopy, vol. 13, No. 3, Jun. 1997 pp. 332–339.

*Primary Examiner*—Michael Buiz
*Assistant Examiner*—David O. Reip
*Attorney, Agent, or Firm*—Pandiscio & Pandiscio

[57] ABSTRACT

A drill guide assembly for producing a tunnel in a bone comprises a rack having a probe portion for engagement with a desired bony landmark, and a tool holder portion for holding tools for penetrating the bone. The probe portion is provided with an orifice therethrough. The tool holder portion is adapted to retain the tools for penetrating the bone, such that an extension of the axis of a tool passes through the orifice.

45 Claims, 14 Drawing Sheets

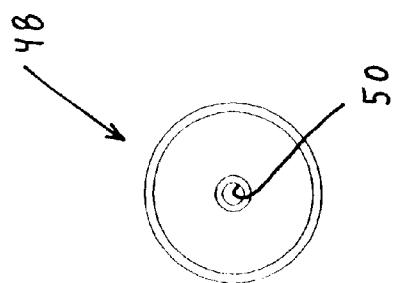
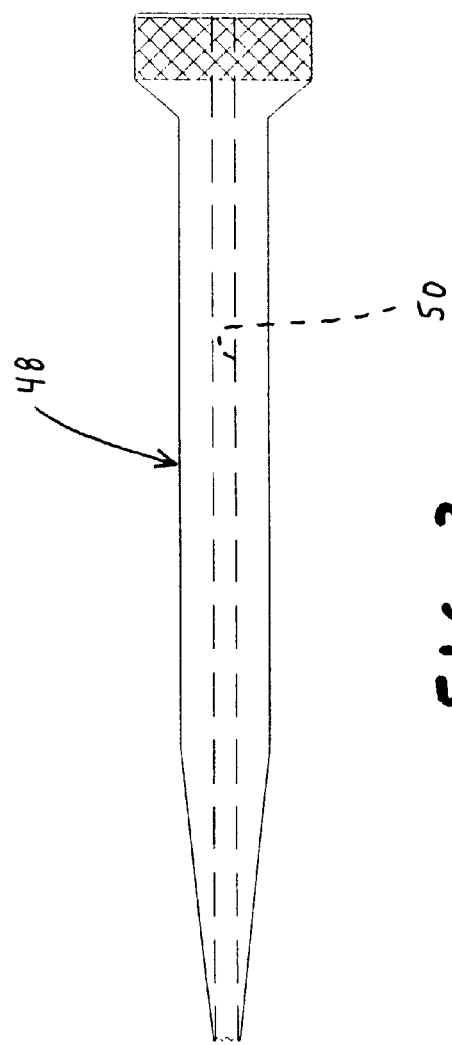

DRILL GUIDE ASSEMBLY AND METHOD FOR PRODUCING A BONE TUNNEL

FIELD OF THE INVENTION

This invention relates to surgical devices and procedures in general, and more particularly to drill guide assemblies and methods for producing tunnels in bones.

BACKGROUND OF THE INVENTION

The anterior and posterior cruciate ligaments of the human knee cooperate with other ligaments and soft tissue to provide static and dynamic stability to the joint. Often, the anterior cruciate ligament (ACL) is ruptured or torn as a result of, for example, sports related activities. Consequently, various surgical procedures have been developed for reconstructing the ACL and restoring normal function to the knee.

In many instances, the ruptured ACL is replaced by substituting a harvested or synthetic graft ligament. More particularly, a graft ligament is extended across the interior of the joint and its two opposing ends are anchored to the femur and tibia bones, respectively. Typically, the graft ends are anchored by first forming bone tunnels in the femur and tibia, then extending the graft ends either part way or all the way through the bone tunnels in the femur and tibia, and then making the graft ends fast, either to the side walls of the bone tunnels or to the exterior surfaces of the bones. The graft is anchored in place by means well known in the art. Once fixed in position, the graft cooperates with the surrounding tissues and replaces the damaged ACL.

It will be appreciated that there is a complex interdependency between the ACL and the other knee ligaments, bones and soft tissues. Consequently, the precise positioning of the graft ACL relative to the surrounding bones is critical to successful reconstruction of the knee joint. In particular, the positioning and formation of the bone tunnels must be precisely controlled by the surgeon.

In U.S. Pat. No. 4,672,957 to Hourahane; U.S. Pat. No. 4,722,331 to Fox; U.S. Pat. No. 4,739,751 to Sapega et al.; U.S. Pat. No. 4,781,182 to Purnell et al.; U.S. Pat. No. 4,920,958 to Walt et al.; U.S. Pat. No. 5,112,337 to Paulos et al.; U.S. Pat. No. 5,154,720 to Trott et al.; and U.S. Pat. No. 5,163,940 to Bourque, there are disclosed a variety of drill guide means for forming a positioned tunnel in the bones of a knee joint, or the like. The foregoing patents further disclose several different methods for using such drill guides.

Drill guide devices, such as those taught in the above-referenced patents, generally comprise a housing having an axial opening, a probe connected to the housing and having a tip that is adapted to be disposed within the interior of the knee at the distal point where one end of the tunnel is to exit the target bone, and a guidewire sleeve for directing a guidewire into position on the anterior surface of one of the bones of the knee joint. The housing is connected to the probe by an adjustable rack that is generally of a circular arc configuration. The housing is arranged so that its axial opening is more or less aligned to intersect with the aforementioned probe tip, and the guidewire sleeve is generally slidable or variable in position within the housing's axial opening. The relative angular position of the probe and the guidewire sleeve contained within the housing is slidably adjustable on the rack. All of the aforementioned parts are held in relation to one another by releasable locking means known in the art.

In ACL reconstruction, the known drill guide devices are used by first placing the probe tip at or near a predetermined location on the tibial plateau. Next, the guidewire sleeve is both angularly and longitudinally adjusted relative to the probe tip so that the distal end of the guidewire sleeve is directed toward the appropriate position on the anterior surface of the tibia. Once in place, the probe tip and guidewire sleeve are locked in position relative to each other by the aforementioned known locking means. Preferably, the probe tip and guidewire sleeve are locked into position while compressively engaging the tibia from two opposing directions, whereby the drill guide will be secured in proper position relative to the tibia.

Once the guidewire sleeve is adjusted and locked in position, a guidewire is slid through the guidewire sleeve and advanced (e.g., by drilling or tapping) through the tibia. The guidewire defines the tibial tunnel drilling axis. When the guidewire is seated in position in the tibia, the guidewire sleeve is unlocked and removed, longitudinally, back along the guidewire. The housing, probe and rack are then removed, leaving the guidewire embedded in the tibia. A cannulated drill bit is then slid over the guidewire to drill the tibial tunnel according to methods known to those skilled in the art. Thus, the tibial tunnel is drilled after the drill guide device has been removed from the patient. In other words, the drill guide device serves only to emplace the guidewire, and it is removed before the cannulated drill bit is introduced onto the guidewire.

It should be appreciated that, with the foregoing arrangement, while the position of the guidewire itself in the tibia is well set, in some situations the cannulated drill bit may be oriented in a manner in which the axis thereof fails to coincide with the axis of the guidewire in the tibia, leading to damage in the guidewire and the production of a tunnel not entirely consistent with the placement of the guidewire.

Further, coring drill bits are sometimes used to obtain a core of bone while producing the tibial tunnel, for purposes of later using that core to anchor a graft or to fill previously created bone defects from graft harvesting. The coring drill is generally a tubular structure with cutting teeth at the distal end. The internal diameter of the coring drill is much greater than the external diameter of the guidewire. As such, the current coring drill bits generally fail to provide adequate centering about the guidewire at the distal end of the coring drill. On occasion the guidewire may actually bend to the point where the coring drill bit's distal end cutting teeth cut across the guidewire itself.

Also, when coring drill bits are used to obtain a bone core while producing the tibial tunnel, on occasion the core is lost or damaged by virtue of slipping from the bit and falling or, conversely, by the inability to coax the core out of the bit.

Accordingly, there exists a need for a drill guide assembly having means for connecting the distal end of the guidewire to the tip of the probe so as to render the drill guide assembly more stable after the guidewire has been placed in the bone and the guidewire sleeve removed.

There also exists a need for an improved drill guide assembly in which the assembly may be left in place about the tibia while the bone tunnel is formed in the tibia.

There further exists a need for a drill guide assembly in which the coring drill can be properly centered about the guidewire during drilling.

There also exists a need for a drill guide assembly in which a bone core captured in a coring drill bit may be safely retained in the bit until needed, and then may be thereafter easily removed.

OBJECTS OF THE INVENTION

Accordingly, one object of the present invention is to provide an improved drill guide assembly having a facility for interconnecting the distal end of the guidewire and the tip of the probe as the distal end of the guidewire emerges from the bone.

Another object of the present invention is to provide an improved drill guide assembly wherein the assembly includes means for properly centering the distal end of the drill bit about the guidewire.

Yet another object of the present invention is to use the drill guide assembly's housing as a guide for the coring drill.

A further object of the present invention is to provide an improved drill guide assembly having a facility for capturing a bone core in a drill bit, retaining the bone core in isolation until needed, and then removing the bone core from the drill bit.

A still further object of the present invention is to provide an improved method for producing a tunnel in a bone.

SUMMARY OF THE INVENTION

These and other objects of the present invention are addressed by the provision and use of a novel drill guide assembly for producing a tunnel in a bone, the assembly comprising a rack having a probe portion for engagement with a desired bony landmark, and a tool holder portion for holding tool means for penetrating the bone, the probe portion having an orifice therethrough. The tool holder portion is adapted to retain the tool means such that an extension of the axis of the tool means passes through the probe orifice.

The objects of the present invention are further addressed by the provision and use of a novel drill guide assembly for producing a tunnel in a bone and preserving a bone core resulting from the tunnel production, the assembly comprising a rack having a probe portion for engagement with a desired bony landmark, and a tool holder portion for holding tool means for penetrating the bone. The tool means includes a coring drill bit adapted for fixing to the tool holder portion of the rack, the bit having teeth at a first end thereof, the first end of the bit being adapted to receive a collar mounted between the first end of the bit and the bone, wherein the collar is mounted on a guidewire extending through the bit and the bone. The tool holder portion of the rack is adapted to fit snugly with the coring drill bit but allow slidable translation along, and rotation about, the longitudinal axis of the coring drill bit. The bit is adapted to permit sliding movement of the collar in the bit as the bit enters the bone and a drilled-out core portion of the bone extends progressively into the bit.

The objects of the present invention are further addressed by the provision and use of an alternative novel drill guide assembly for producing a tunnel in a bone and preserving a bone core resulting from the tunnel production, the assembly comprising a rack having a probe portion for engagement with a desired bony landmark, and a tool holder portion for holding tool means for penetrating the bone, the probe portion having an orifice therethrough, and the tool holder portion being adapted to retain the tool means for penetrating the bone and in such a manner that an extension of the axis of the tool means passes through the orifice. The assembly further comprises locking means for securing together the rack and tool holder portions, the latter being provided with a bore therethrough for guiding and/or securing the tool means, comprising bone boring means, in the tool holder portion. The assembly further comprises adapter means for disposition in the bore, the bone boring means being receivable by the adapter means, the bone boring means comprising a coring drill bit receivable by the adapter means and a guidewire receivable by the drill bit. The locking means for securing the bone boring means in the tool holder portion comprises screw means for locking the adapter means in the bore and for locking the drill bit in the adapter.

The objects of the present invention are further addressed by the provision and use of a plunger for insertion into the drill bit for pushing the collar distally along the interior of the drill bit and, thereby, pushing the excised bone core out of the drill bit.

The objects of the present invention are still further addressed by the provision and use of a cylinder having open first and second ends, the second end of the cylinder being adapted to receive and retain the coring drill bit therein with the first end of the drill bit spaced from the first end of the cylinder, whereby movement of the excised bone core out of the drill bit causes the bone core to enter an otherwise unoccupied portion of the cylinder adjacent to the first end of the cylinder and to be loosely retained by the cylinder until removal of the bone core from the cylinder through the first end of the cylinder.

The objects of the present invention are still further addressed by the provision and use of a novel method for producing a tunnel in a bone, the method comprising the steps of:

(1) providing a drill guide assembly comprising a rack having a probe portion for engagement with a desired bony landmark, and a tool holder portion for holding tool means for penetrating the bone, wherein the probe portion has an orifice therein, and the tool holder portion is adapted to hold the tool means such that an extension of the axis of the tool means passes through the orifice, and further wherein the tool means comprise a guidewire sleeve for connection to the tool holder portion of the rack, a guidewire for extending axially through the guidewire sleeve, and a coring drill bit adapted for connection to the tool holder portion of the rack, and collar means for mounting on the guidewire;

(2) fixing the guidewire sleeve to the tool holder portion of the rack;

(3) sliding the guidewire through the guidewire sleeve;

(4) sliding the collar means onto the guidewire at a distal end of the guidewire;

(5) engaging a desired bony landmark on an end surface of the bone with the probe portion;

(6) moving the distal end of the guidewire and the collar means into engagement with the bone;

(7) passing the guidewire through the bone and through the orifice in the probe portion of the rack;

(8) removing the guidewire sleeve from the tool holder portion of the rack;

(9) mounting the coring drill bit on the tool holder portion of the rack, with the guidewire extending through the bit and with the cutting end of the bit adjacent to the collar means which is adjacent to the bone; and

(10) advancing the bit into the bone, with the collar means being forced into the bit and thereafter progressively further into the bit, as the bit advances into the bone, and with the bone core cut by the bit entering the bit, whereby to produce the desired tunnel in the bone and to capture the bone core produced thereby.

In accordance with a further novel feature of the present invention, the above method includes the additional steps of:

(11) detaching the bit from the tool holder portion of the rack and from the guidewire; and

(12) providing a plunger insertable into a second end of the bit, and inserting the plunger into the bit through the second end of the bit to push the collar means toward the cutting end of the bit to move the bone core out of the bit.

In accordance with a still further novel feature of the present invention, the above method includes the additional step of:

(13) providing a cylinder having first and second open ends, the second end being adapted to receive and retain the bit, and placing the bit in the cylinder with the second end of the bit proximate to and retained by the second end of the cylinder, whereby, upon moving the bone core out of the bit, the bone core enters a portion of the cylinder not occupied by the bit.

The objects of the present invention are still further addressed by the provision and use of an alternative novel method for producing a tunnel in a bone, the method comprising the steps of:

(1) providing a drill guide assembly comprising a rack having a probe portion for engagement with a desired bony landmark, and a tool holder portion for holding tool means for penetrating the bone, the probe portion having an orifice therein, the tool holder portion being adapted to hold the tool means with an extension of the axis of the tool means passing through the orifice, the tool means comprising a guidewire sleeve for connection to the tool holder portion of the rack, the tool means further comprising a coring drill bit adapted for connection to the tool holder portion of the rack, a guidewire for extending axially through the guidewire sleeve and the drill bit, respectively, and collar means for mounting on the guidewire;

(2) engaging a desired bony landmark on an end surface of the bone with the probe portion;

(3) fixing the guidewire sleeve to the tool holder portion of the rack;

(4) moving the distal end of the guidewire sleeve into engagement with the bone;

(5) sliding the guidewire through the guidewire sleeve;

(6) extending the guidewire through the bone and through the orifice in the probe portion of the rack;

(7) removing the guidewire sleeve from the tool holder portion of the rack;

(8) sliding the collar means onto the guidewire from a proximal end of the guidewire and positioning the collar means proximate the bone;

(9) attaching the coring drill bit to the tool holder portion of the rack, with the guidewire extending through the drill bit and a cutting end of the drill bit adjacent to the collar means which is proximate the bone; and

(10) advancing the drill bit into the bone, with the collar means being forced into the drill bit, and progressively further into the drill bit as the drill bit advances into the bone, and a bone core cut by the drill bit enters the drill bit;

whereby to produce the tunnel in the bone and capture the bone core produced thereby.

The objects of the present invention are still further addressed by the provision and use of another alternative novel method for producing a tunnel in a bone, the method comprising the steps of:

(1) providing a drill guide assembly comprising a rack having a probe portion for engagement with a desired bony landmark, and a tool holder portion for holding tool means for penetrating the bone, the probe portion having an orifice therein, the tool holder portion being adapted to hold the tool means with an extension of the axis of the tool means passing through the orifice, the tool means comprising a coring drill bit for connection to the tool holder portion of the rack, the tool means further comprising a guidewire adapted to extend axially through the drill bit, and collar means for mounting in the drill bit and in which is mountable the guidewire;

(2) engaging a desired bony landmark on an end surface of the bone with the probe portion;

(3) connecting the coring drill bit, with the collar means therein, to the tool holder portion;

(4) moving the coring drill bit into engagement with the bone;

(5) locking the coring drill bit to the tool holder portion to prevent movement of the drill bit in the tool holder;

(6) passing the guidewire through the collar means in the drill bit;

(7) drilling the guidewire through the bone, passing a distal end of the guidewire through the probe orifice;

(8) unlocking the coring drill bit to permit movement of the drill bit in the tool holder portion; and (9) rotating the coring drill bit to cut the tunnel through the bone.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 3 is a side elevational view of a guidewire sleeve used in conjunction with the drill guide rack shown in FIGS. 1 and 2;

FIG. 4 is a head end elevational view of the guidewire sleeve of FIG. 3;

DETAILED DESCRIPTION OF THE PREFERRED EMBODIMENTS

Figure 1:
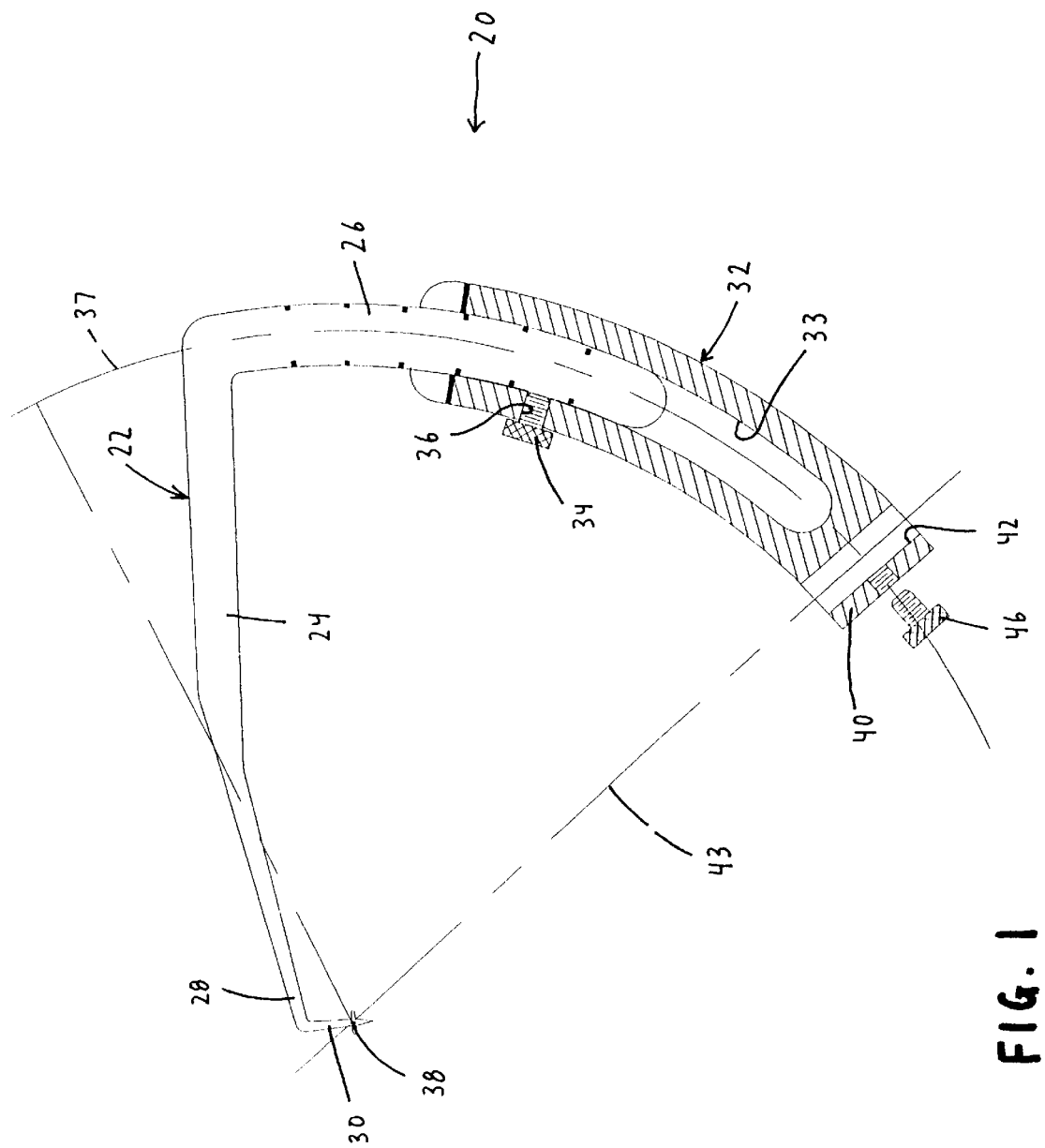
FIG. 1 is a side elevational view, partly in section, of a rack portion of a drill guide assembly formed in accordance with the present invention.

Referring first to FIG. 1, it will be seen that one illustrative drill guide assembly includes a rack 20 provided with a first guide member 22 having a first arm portion 24 and a second arm portion 26 extending from first arm portion 24. Second arm portion 26 is generally perpendicular to first arm portion 24 and is curved. For ACL corrective procedures, approximate perpendicularity of second arm portion 26 to first arm 24 usually is preferred, but other angles may be selected in accordance with other anatomical considerations in other corrective procedures. First arm portion 24, at a free end 28 thereof, is provided with a probe 30 for engagement with a bone, such as a tibia, in ACL procedures, as will be described hereinafter.

Figure 2:
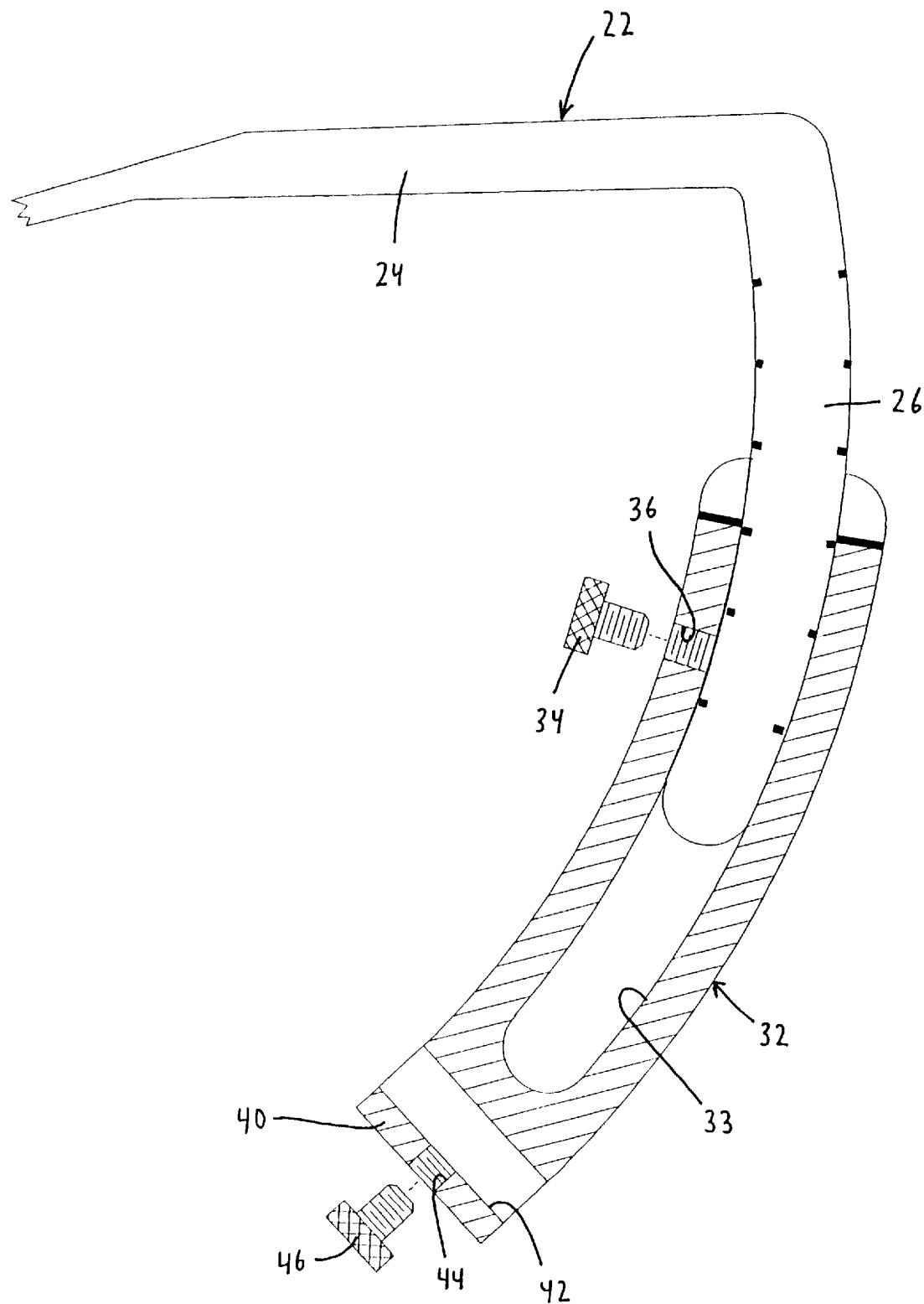
FIG. 2 is an enlarged side elevational view, partly in section, of selected portions of the rack portion of FIG. 1.

A second guide member 32 is slidably disposed on second arm portion 26 of first guide member 22, with second guide member 32 being complementarily curved. Preferably, second arm portion 26 of first guide member 22 is slidingly received in a curved groove 33 in second guide member 32. Locking means are provided to lock second arm portion 26 in second guide member 32. Preferably, these locking means take the form of a first thumb screw 34 threadedly disposed in a threaded hole 36 in second guide member 32 (FIG. 2) and adapted to bear against second arm portion 26 of first guide member 22.

Figure 5A:
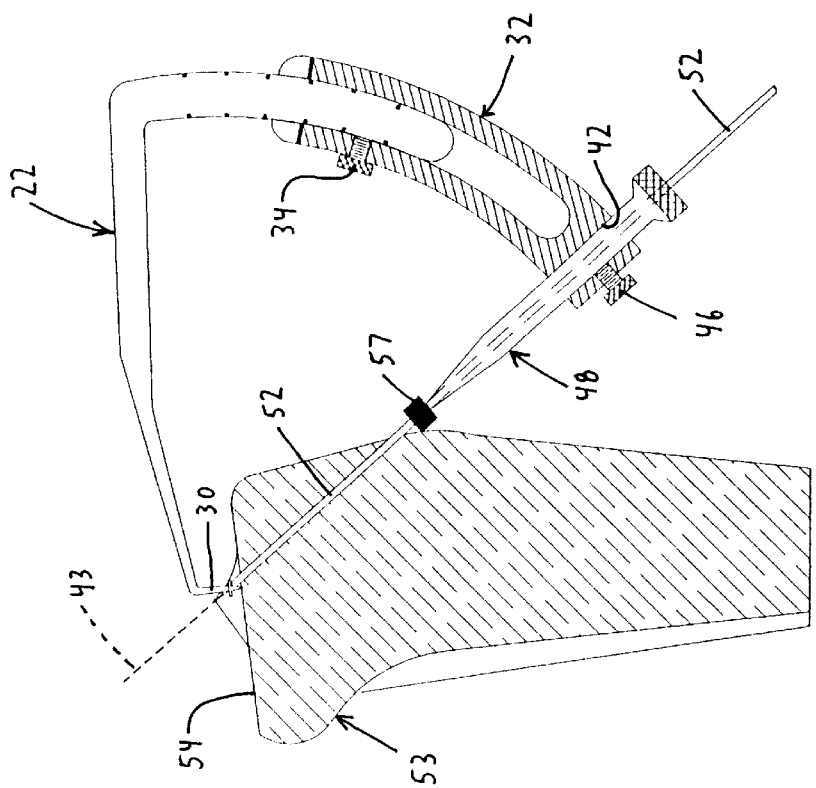
FIG. 5A is a view similar to FIG. 5, but shows the guidewire sleeve advanced so as to abut the first collar member and the guidewire advanced through a bone.
Figure 7:
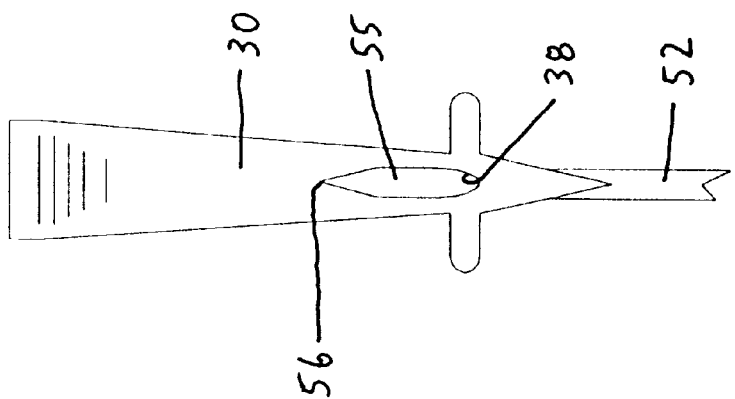
FIG. 7 is a front elevational view of the portion of the assembly shown in FIG. 6, taken along line 7—7 of FIG. 6.

The curve of second arm portion 26 of first guide member 22 defines a circle 37 (FIG. 1). The curved second guide member 32 is disposed in the same circle 37. The probe 30 on free end 28 of first guide member 22 is provided with an orifice 38 therethrough (FIGS. 6 and 7). Second guide member 32, near a free end 40 thereof (FIG. 2) is provided with a bore 42 therethrough. Bore 42 is disposed so that an extension of the axis 43 of bore 42 passes through orifice 38 of probe 30 (FIGS. 1, 5, 5A, and 6). The orifice 38 is at the center of circle 37. It will thus be understood that orifice 38 is always aligned with the axis of bore 42, and is thereby aligned with the axis of any tool held in bore 42, regardless of the setting selected for second arm portion 26 in groove 33 of second guide member 32. Bore 42 of second guide member 32 serves as a tool holder and is adapted to receive tools, such as bone boring means, to be described hereinafter. Free end 40 of second guide member 32 is provided with a threaded hole 44 (FIG. 2) for receiving a second thumb screw 46 which is adapted to enter bore 42 to engage the aforementioned bone boring means so as to secure the tools in bore 42.

The bone boring means received by bore 42 includes a guidewire sleeve 48 (FIGS. 3 and 4) having an axial passageway 50 therethrough. The axis of guidewire sleeve passageway 50 coincides with axis 43 of bore 42 when guidewire sleeve 48 is mounted in bore 42, such that the axis of guidewire sleeve 48 passes through orifice 38 of probe 30. The bone boring means further includes a guidewire 52 (FIG. 5) which is receivable by, and movable through, guidewire sleeve passageway 50. The guidewire 52 coincides with axis 43 of bore 42 and is, therefore, aligned with probe orifice 38 when guidewire 52 is mounted in guidewire sleeve 48. Guidewire 52 can be passed through a tibia 53 (FIG. 5A), e.g. by drilling or tapping, until guidewire 52 emerges from the tibial plateau 54 and extends through probe orifice 38 (FIGS. 5A, 6 and 7). Guidewire 52 includes a distal end 55 which terminates in a point 56 (FIGS. 6 and 7).

Figure 5:
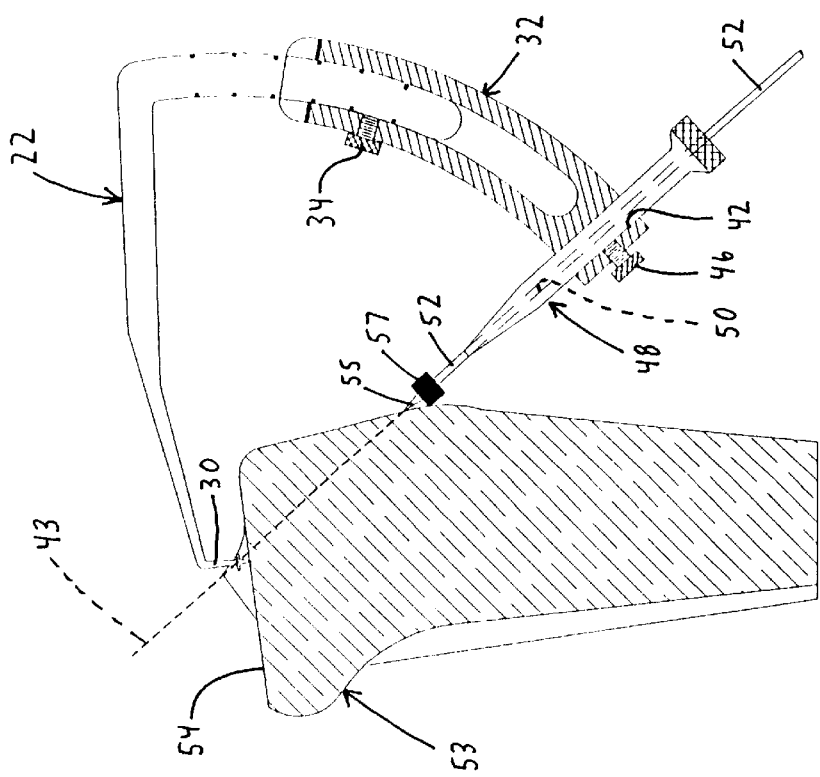
FIG. 5 is a side elevational view, partly in section, of a drill guide assembly including the drill guide rack of FIGS. 1 and 2 and the guidewire sleeve of FIGS. 3 and 4, combined with a guidewire and a first collar member.
Figure 6:
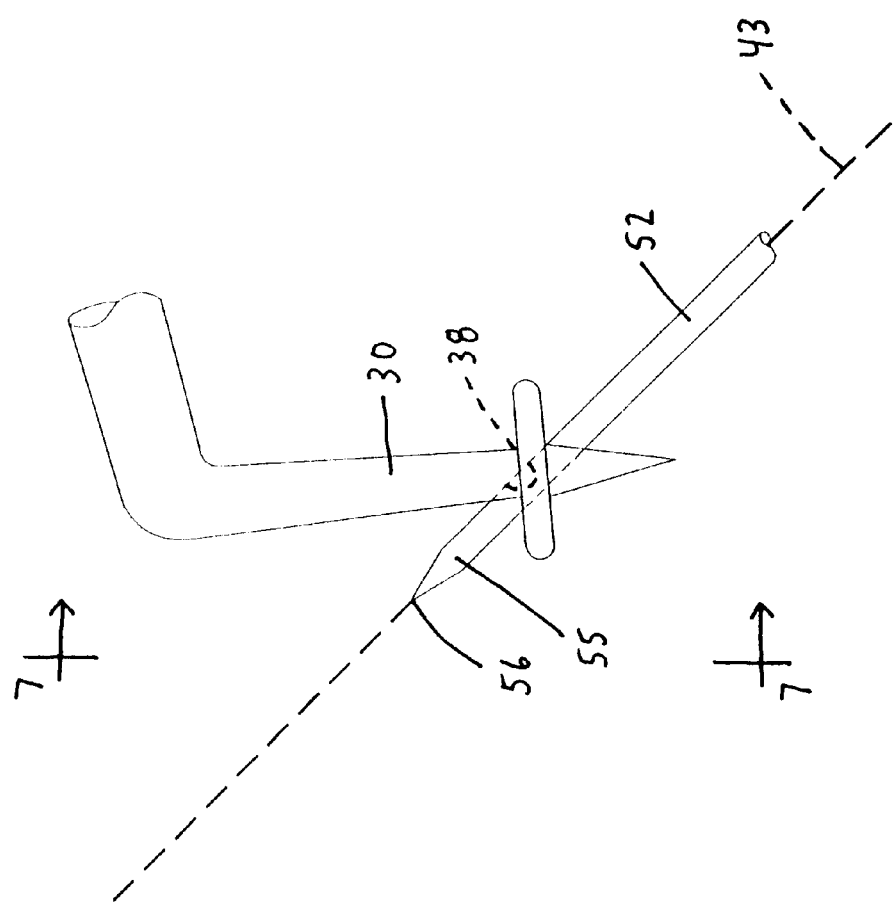
FIG. 6 is an enlarged side elevational view of a portion of the assembly of FIG. 5A.

Referring to FIG. 5, it will be seen that the assembly includes a first collar 57 which has a central opening 51 therethrough (FIG. 23) and which may be slipped over distal end 55 of guidewire 52 and, referring to FIG. 5A, may serve to provide support to guidewire 52 adjacent to tibia 53 during advancement of guidewire 52 into, and through, the tibia. First collar 57 is preferably formed of a metal, or rigid plastic material, or a composite thereof, having a low coefficient of friction.

Figure 8:
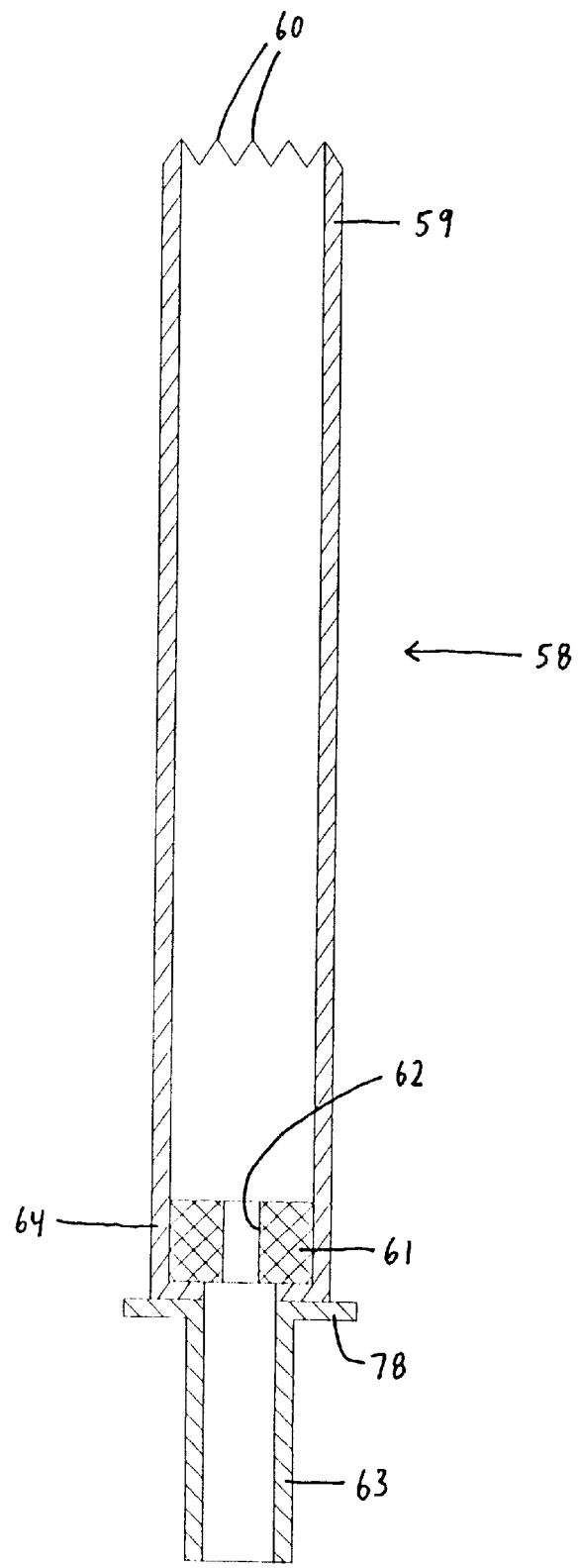
FIG. 8 is a centerline sectional view of a coring drill used in conjunction with the drill guide assembly of FIGS. 1 and 2.
Figure 9:
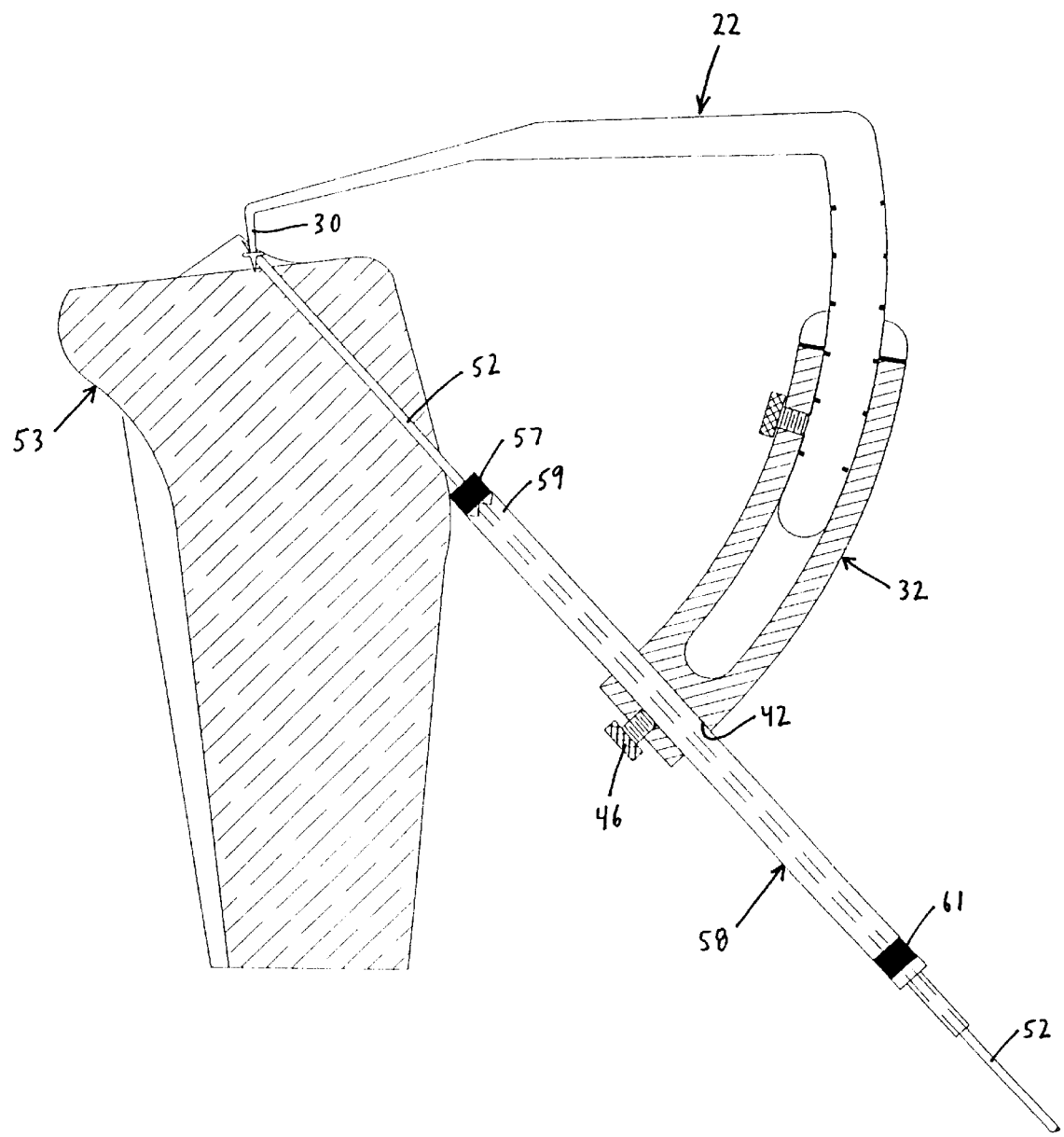
FIG. 9 is a view similar to FIG. 5, but shows the coring drill, rather than the guidewire sleeve, in combination with the drill guide assembly.
Figure 10:
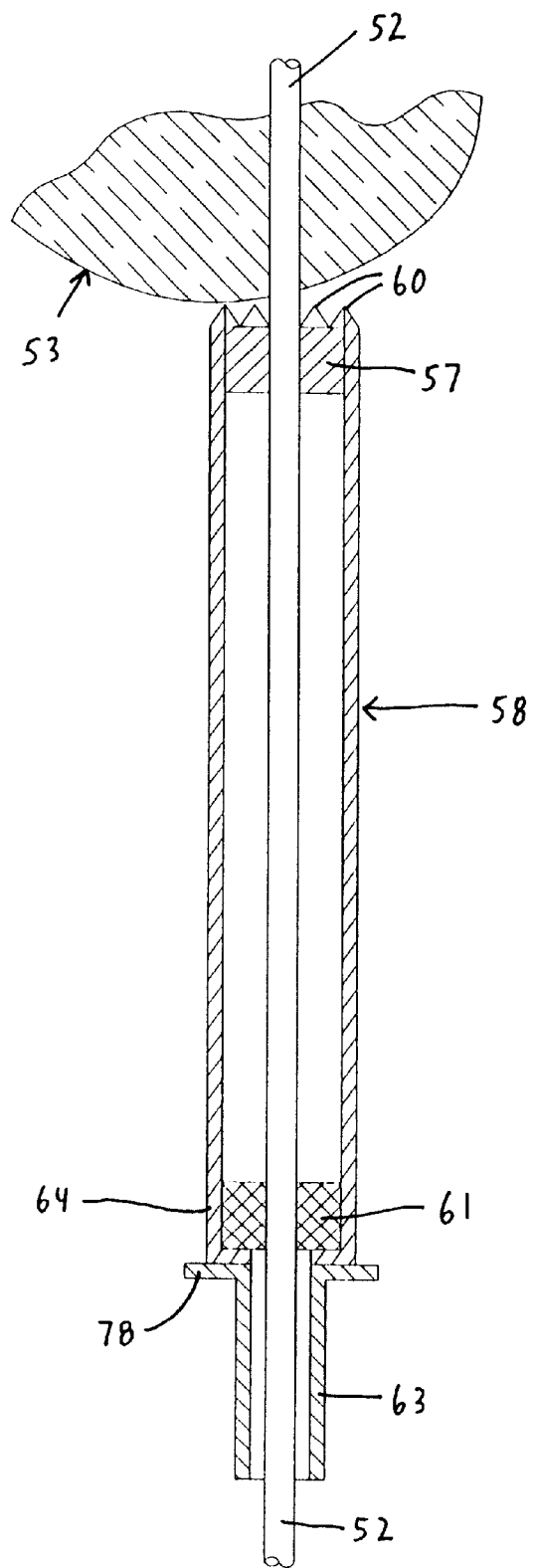
FIG. 10 shows the coring drill after it has been advanced against the bone, with the first collar member having entered the coring drill.

The aforementioned bone boring means further includes a coring drill bit 58 (FIG. 8) receivable by and mountable in bore 42 of second guide member 32 (FIG. 9). In one mode of use, which will be discussed in further detail below, guidewire 52 is first passed through guidewire sleeve 48 (which is mounted in rack bore 42) and through first collar 57. Then probe 30 is positioned at the targeted bony landmark on the tibial plateau 54, and guidewire 52 is advanced so as to engage tibia 53. Rack 20 is then made fast with thumb screw 34. See FIG. 5. Then guidewire 53 is passed through tibia 53. See FIG. 5A. After guidewire 52 has been advanced through tibia 53, and through orifice 38 of probe 30, guidewire sleeve 48 is backed off guidewire 52. Then the coring drill bit 58 is mounted on guidewire 52 and placed in bore 42. At a first end 59 thereof, drill bit 58 is provided with teeth 60 (FIG. 8) for penetrating bone. Drill bit 58 is of a cylindrical, tubular configuration so as to "core" the bone and receive the cut bone core within the bit. Such bits are commonly referred to as "coring bits". The drill bit 58 is provided with a second collar 61 having a central opening 62 (FIG. 23) therethrough for receiving guidewire 52 (FIG. 10). A stem portion 63 extends from a second end 64 of drill bit 58, and this stem portion is hollow to permit passage therethrough of guidewire 52. Thus, guidewire 52 passes completely through drill bit 58 and the drill bit is permitted axial and rotative movement in rack bore 42. The second collar 61 preferably is at, or near, second end 64 of drill bit 58, and preferably is formed of metal, rigid plastic, or a composite thereof, having a low coefficient of friction.

Figure 11:
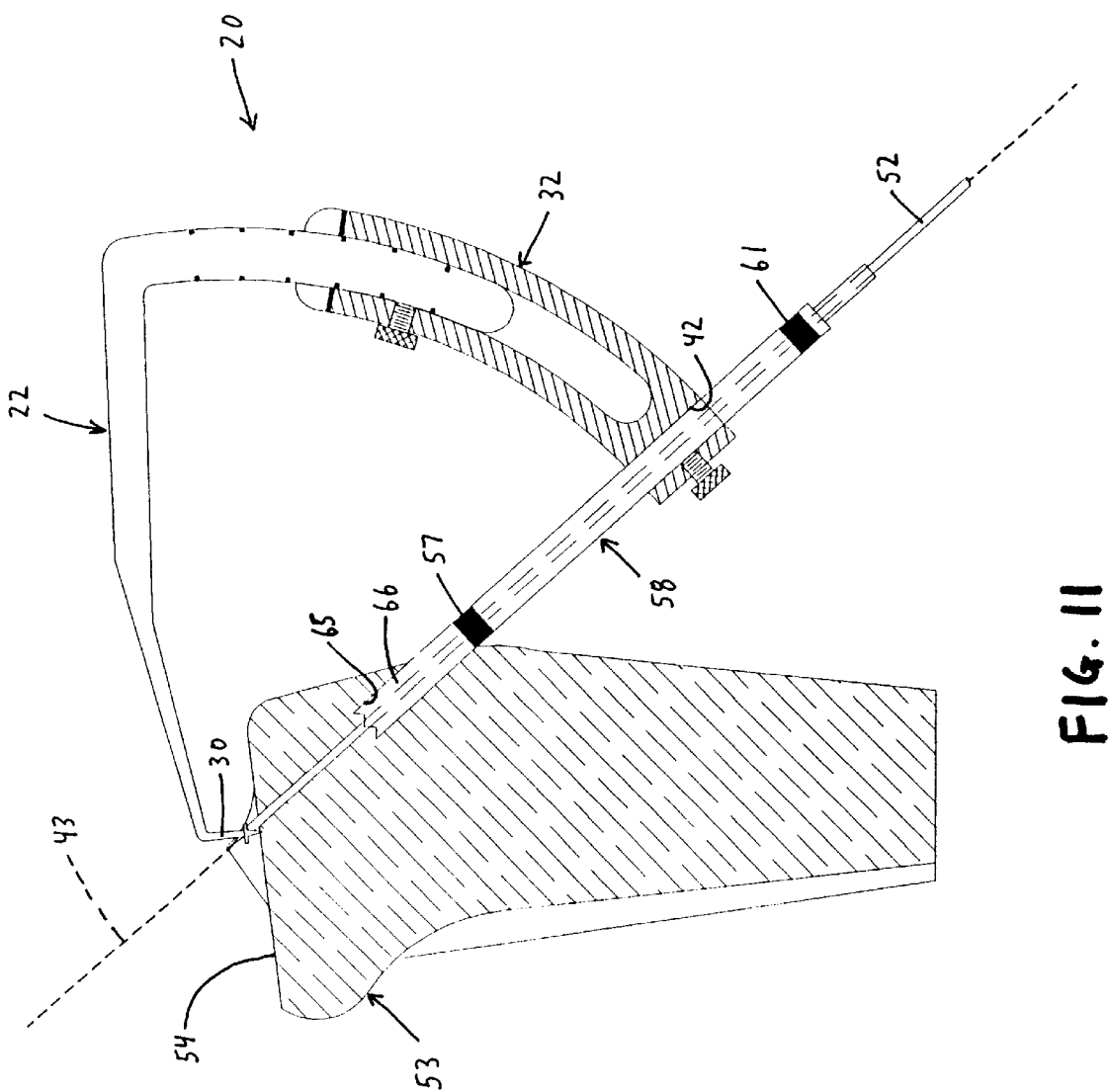
FIG. 11 is a view similar to FIG. 9, but shows the coring drill having advanced into the bone.

The drill bit 58 is placed such that first end 59 thereof rests against first collar 57 (FIG. 9) which, in turn, rests against tibia 53. Drill bit 58 is then moved forwardly against the tibia, whereupon first collar 57 enters drill bit 58 (FIG. 10). At about the same time, a drill (not shown) which has been applied to stem portion 63 of bit 58 rotates the bit so as to cause the bit to cut into the tibia, thereby creating a bone tunnel 65 (FIG. 11) in the tibia and receiving a tibia core 66 within drill bit 58. As drill bit 58 advances through tibia 53, progressively more and more of bone core 66 is received in drill bit 58 and first collar 57 moves progressively rearwardly. Inasmuch as drill bit 58 is aligned with bore axis 43, tunnel 65 tracks precisely along the path of guidewire 52. The support provided by bore 42 and the first collar 57 prevents the drill bit from deviating from the intended path. The engagement of the distal end 55 of the guidewire 52 with the orifice 38 of the probe 30 assures constant alignment of the axis 43 of bore 42 relative to the targeted bony landmark on the tibial plateau 54. In due course, tunnel 65 is extended completely through the tibia, exiting through tibial plateau 54, aligned with orifice 38 in probe 30.

Upon completion of the tunnel cutting operation, drill bit 58, with bone core 66 therein, is backed off guidewire 52 and out of the rack's tool holder means 42.

Figure 12:
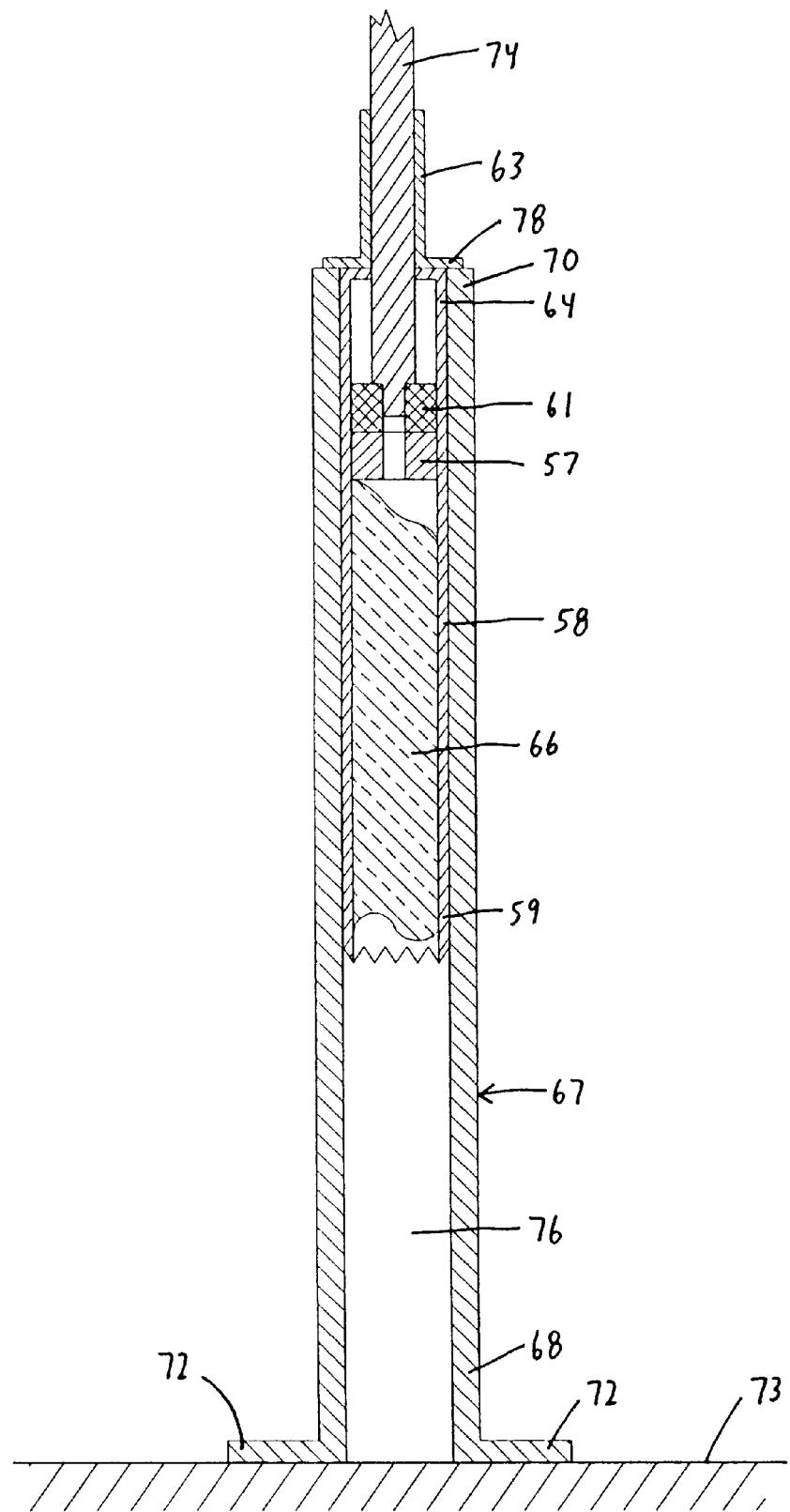
FIG. 12 illustrates a cylinder adapted to receive the coring drill therein and a plunger adapted to push the excised bone core from the coring drill.

To assist in removing tibial bone core 66 from drill bit 58, and in preserving the bone core until needed, there is provided a cylinder 67 (FIG. 12) having an open first end 68 for discharge of bone core 66 and an open second end 70 for receiving drill bit 58 with bone core 66 and collars 57 and 61 therein. First end 68 of cylinder 67 preferably is provided with a flange 72 by which cylinder 67 may be rested on a flat surface 73 and remain stable without attachment to that surface.

To urge bone core 66 from drill bit 58, there is provided a plunger 74 which is received by drill bit stem portion 63 and which engages collar 61 and pushes collars 61 and 57 along the interior of drill bit 58 (FIG. 13) toward first end 59 of drill bit 58 so as to push bone core 66 into a portion 76 of cylinder 67 which is otherwise unoccupied. The excised bone core 66 remains in cylinder portion 76 until needed. Alternatively, bone core 66 may be left in drill bit 58 until needed, and plunger 74 used to extract the core from the bit, with or without use of cylinder 67.

Figure 13:
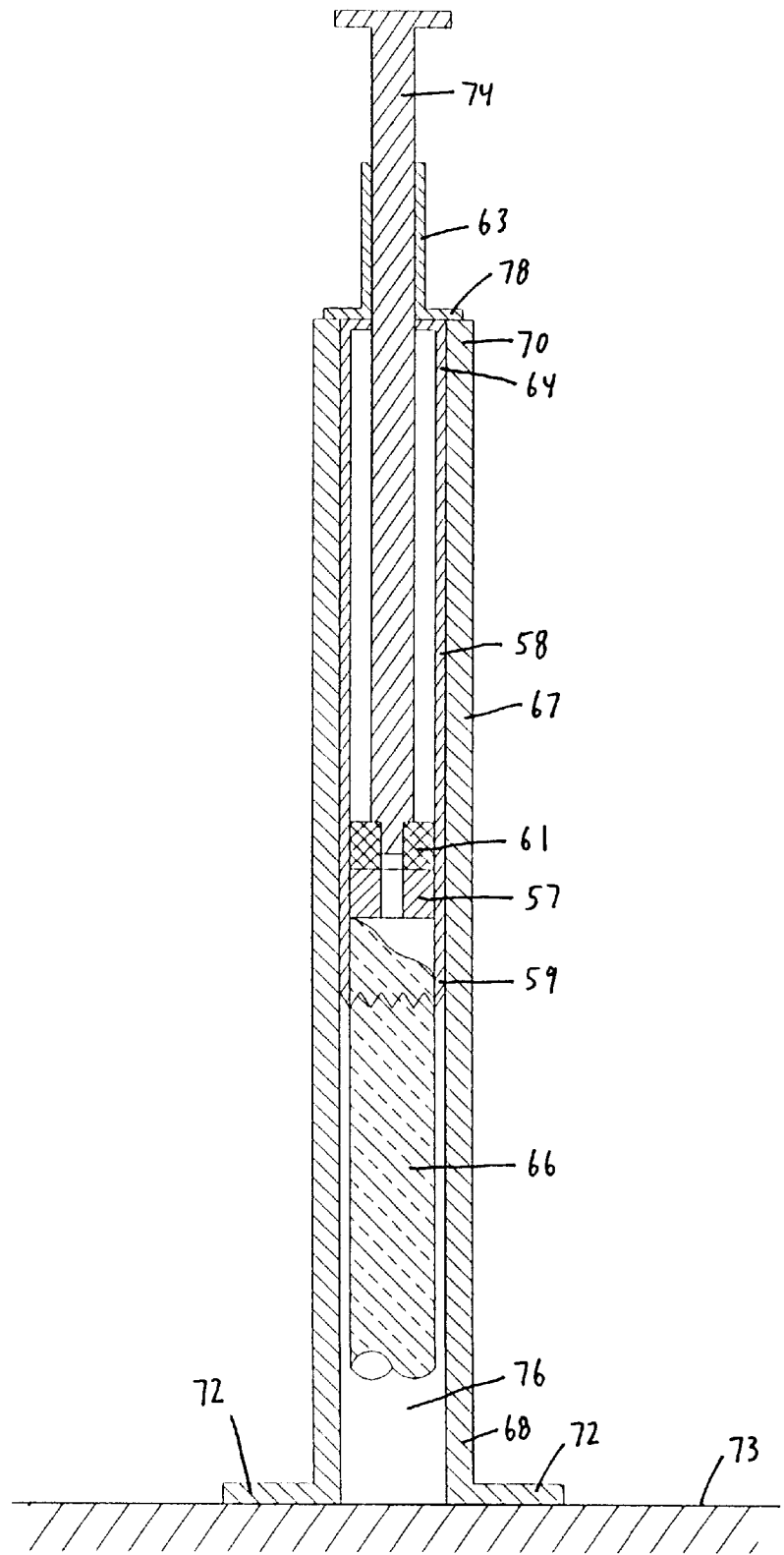
FIG. 13 is a view similar to FIG. 12, but shows the bone core being pushed from the coring drill by the plunger.

Drill bit 58, at second end 64 thereof, is provided with a flange 78 (FIGS. 8, 10, 12 and 13) which extends beyond the side walls of the drill bit and supports drill bit 58 in cylinder 67 (FIG. 13).

In one form of the invention, the foregoing apparatus is intended to be used as follows.

Guidewire sleeve 48 is first fixed to the rack's tool holder portion (FIG. 5) by securing guidewire sleeve 48 in bore 42 of second guide member 32, using thumb screw 46 to lock guidewire sleeve 48 in place. Guidewire 52 is then slid through guidewire sleeve 48. First collar 57 is then slid over distal end 55 of guidewire 52.

Probe 30 is then brought into engagement with a desired bony landmark, such as the tibial eminence of tibial plateau 54 (FIG. 5), and distal end 55 of guidewire 52 and collar 57 are brought into contact with the anterior surface of the tibia. Second guide member 32 is then moved relative to first guide member 22 until an angle desired by the surgeon is reached, at which point thumb screw 34 is tightened down to lock guide members 22 and 32 together.

Guidewire sleeve 48 is then loosened in bore 42, and advanced until the guidewire sleeve bears against collar 57 (which in turn bears against the tibia) and again locked in place (FIG. 5A). If, prior to movement of the guidewire sleeve forwardly, collar 57 is not abutting the tibia, movement of the guidewire sleeve forwardly presses collar 57 against the tibia, supporting guidewire 52 at the point of entry into the tibia.

Guidewire 52, provided with sharp point 56 (FIGS. 6 and 7), is then extended, e.g. by drilling and/or tapping, through the tibia (FIG. 5A) and through orifice 38 in probe 30 (FIGS. 6 and 7).

Thumb screw 46 is then loosened and guidewire sleeve 48 is backed out of bore 42 and off guidewire 52, while the interconnection of guidewire 52 and probe orifice 38 stabilizes the geometry of the guide assembly.

Figures 22, 23:
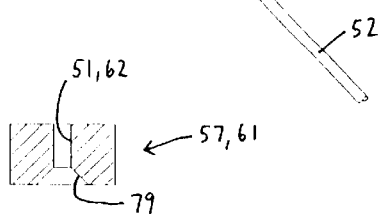
FIG. 22 is a top plan view of the third adapter of FIG. 21.
FIG. 23 is a centerline sectional view of a collar member comprising a portion of the assembly.

Coring drill bit 58 is then mounted in second guide member 32 by placing drill bit 58 in bore 42 (FIG. 9), with guidewire 52 extending through bit 58, collar 61, and cutting end 59 of bit 58 and collar 57. Referring to FIG. 23, it will be seen that the collars 57, 61 are each provided with a frustoconically shaped recess 79 which serves as an entry for guidewire 52, assisting in channeling guidewire 52 into the collar central opening 51, 62.

Coring drill bit 58 is then advanced to engage the tibia (FIG. 10), with collar 57 being forced into the bit. The bit is then advanced into the tibia (FIG. 11), forcing collar 57 further into the interior of the drill bit as the bit advances into the tibia and as the bone core 66 cut thereby enters the bit, whereby to produce tunnel 65 in the tibia and to capture bone core 66 in bit 58. It is to be appreciated that drill bit 58 will remain centered about axis 43 during such cutting, inasmuch as collar 57 provides centering support adjacent the anterior surface of the tibia throughout the drilling operation. It is also to be appreciated that the snug (i.e., close sliding) fit of the drill bit 58 within the bore 42 of second guide member 32 provides additional centering support.

Upon completion of the tunnel drilling operation, drill bit 58 is detached from rack 20 and from guidewire 52, taking bone core 66 with it. Plunger 74 may then be inserted into second end 64 of drill bit 58 (FIGS. 12 and 13) so as to urge collar 61 (and hence also collar 57, which abuts bone core 66) toward the drill bit's first end 59 so as to discharge bone core 66 from the interior of the drill bit.

Alternatively, drill bit 58 may be placed in cylinder 67 before inserting plunger 74, such that when bone core 66 is pushed from the bit, the core will fall into unoccupied portion 76 of cylinder 67, where the bone core 66 remains safely until needed.

In an alternative procedure, probe 30 is engaged with tibia 53, as shown in FIGS. 5 and 5A, but without collar 57 and guidewire sleeve 48 in place. At this point, guidewire sleeve 48 may be absent from the assembly, or may be disposed in bore 42 but backed off from engagement with tibia 53. The first and second guide members 22, 32 are preliminarily set in approximate position. The guidewire sleeve 48 is then placed in bore 42 and advanced to engage tibia 53. The first and second guide members 22, 32 are then adjusted relative to each other, if required, and first and second thumb screws 34, 46 tightened down to lock guide members 22, 32 together and to secure guidewire sleeve 48 in bore 42. The guidewire 52 is then passed through guidewire sleeve 48 and into engagement with tibia 53, and drilled into and through tibia 53, as shown in FIG. 5A. Upon completion of the guidewire drilling operation, screw 46 is loosened and sleeve 48 is backed out of bore 42 and disengaged from guidewire 52. The first collar 57 is then slid onto guidewire 52, through bore 42, and brought into engagement with tibia 53. The drill bit 58 is passed over guidewire 52 and into bore 42 and into engagement with first collar 57, such that first end 59 of drill bit 58 rests against first collar 57 (FIG. 9) which, in turn, rests against tibia 53. Drill bit 58 is then moved forwardly against tibia 53, whereupon first collar 57 enters drill bit 58 (FIG. 10). A drill engaged with drill bit 58 rotates the bit to cause the bit to bite into the tibia and the tibia core 66 to enter the hollow drill bit 58, as described hereinabove.

Figure 14:
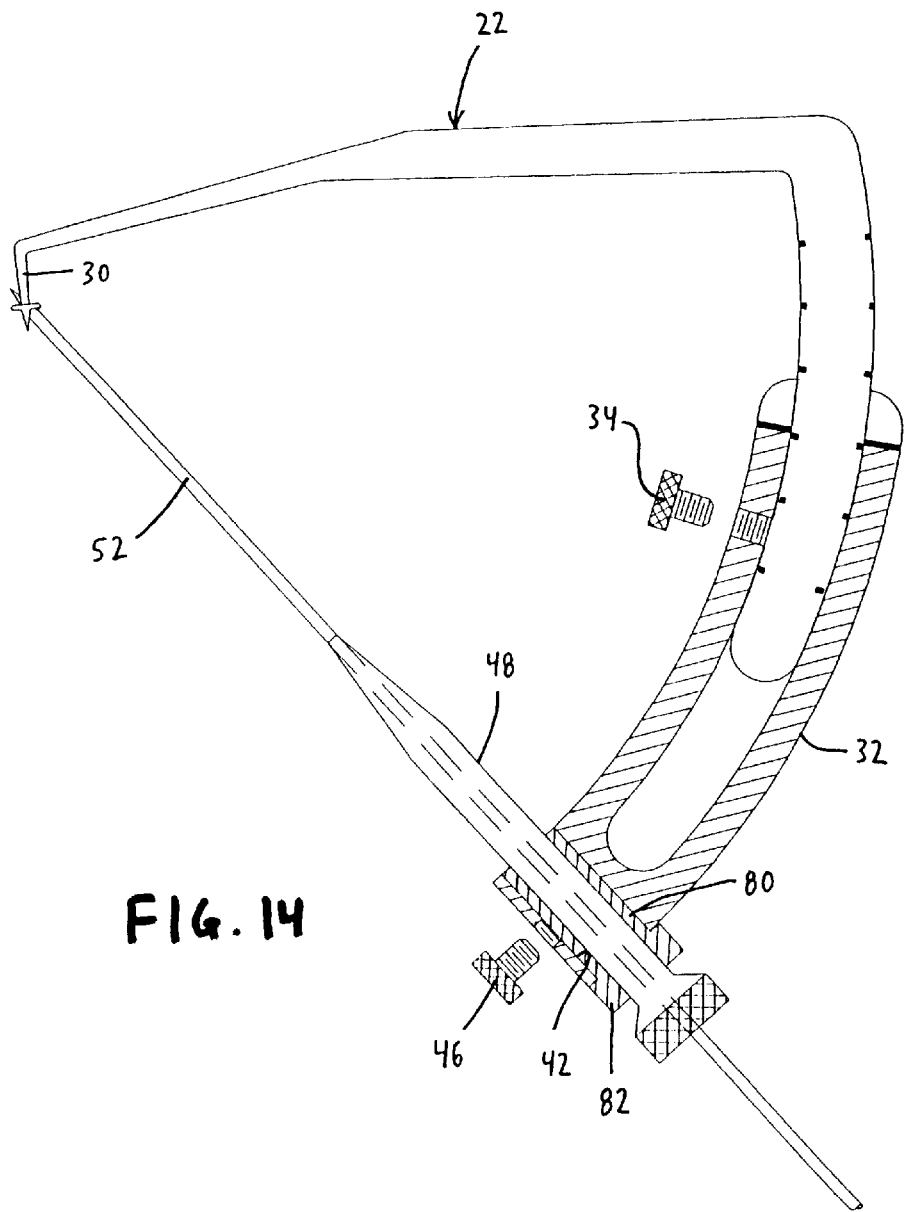
FIG. 14 is a side elevational view, partly in section, of a drill guide assembly illustrative of an alternative embodiment of the invention.
Figure 16:
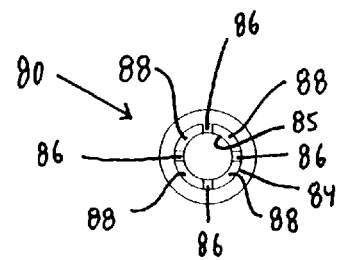
FIG. 16 is a top plan view of the first adapter of FIG. 15.
Figure 17:
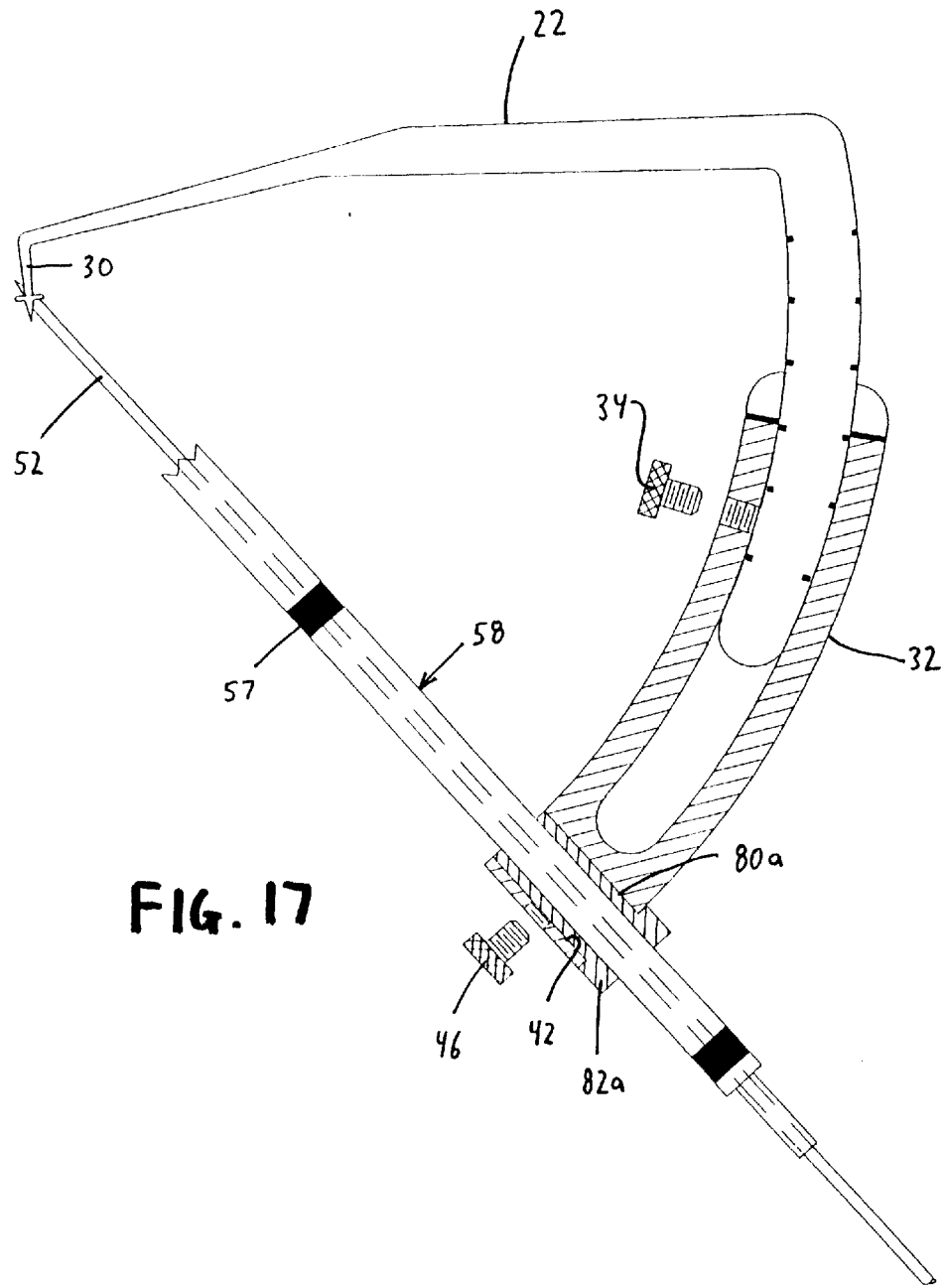
FIG. 17 is a side elevational view, partly in section, of the drill guide assembly of FIG. 14 shown with a second adapter therein.

Referring to FIGS. 14 and 17, it will be seen that in an alternative embodiment, the assembly includes adapters 80 (FIGS. 14–16), 80a (FIGS. 17–19) for disposition in bore 42 and adapted to receive guidewire sleeve 48 and drill bit 58, respectively. While some drill bits are of a diameter equal to the diameter of guidewire sleeve 48, there are drill bits suitable for use in the inventive device and methods presented herein having up to twice the diameter of the guide wire sleeve. Thus, in order for the assembly to accommodate a range of drill bit sizes, the assembly may include a second guide member 32 having bore 42 sized to receive the largest size drill bit and may further include adapter 80a which permits use of smaller-sized drill bits, and includes adapter 80 which permits use of a guidewire sleeve considerably smaller than bore 42.

Figure 15:
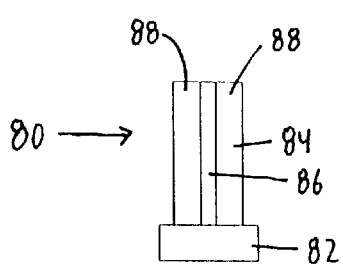
FIG. 15 is a side elevation view of a first adapter for use in the assembly of FIG. 14.

As is shown in FIGS. 15 and 16, adapter 80 includes a head portion 82 and a body portion 84. The body portion 84 is cylindrically shaped with a central bore 85 and provided with slots 86 extending substantially throughout the length of the body portion 84, to define a plurality of fingers 88 upstanding from head portion 82. Upon tightening down of thumb screw 46, the screw pushes one or more fingers 88 inwardly to engage guidewire sleeve 48 to hold sleeve 48 in a stationary mode, such that guidewire 52 may be moved within sleeve 48 without causing movement of sleeve 48 in bore 42.

In operation, adapter 80 is inserted into bore 42, the inner diameter of bore 42 being substantially equal to the outer diameter of adapter 80. The guidewire sleeve 48 is then inserted into the bore 85 of adapter 80, the inner diameter of adapter 80 being substantially equal to the outer diameter of the sleeve 48. After advancing guidewire sleeve 48 to an appropriate position, the sleeve is locked in place by second thumb screw 46. Turning thumb screw 46 causes at least one of the fingers 88 to press against guidewire sleeve 48.

Figure 18:
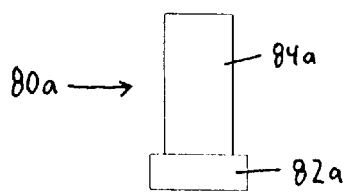
FIG. 18 is a side elevational view of the second adapter of FIG. 17.
Figure 19:
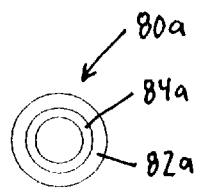
FIG. 19 is a top plan view of the second adapter of FIG. 18.

As is shown in FIGS. 18 and 19, adapter 80a includes a head portion 82a and a body portion 84a. The body portion 84a is cylindrically-shaped. The adapter 80a is provided with an outer diameter substantially equal to the inner diameter of bore 42. The inner diameter of adapter 80a is substantially equal to the outer diameter of drill bit 58.

In operation, adapter 80a is inserted into bore 42 and locked in position by turning thumb screw 46. An adapter 80a is provided for each size drill bit 58, the adapter 80a chaving an inner diameter that matches the outer diameter of the corresponding drill bit. The largest of the drill bits, if matching the diameter of bore 42, does not require the adapter 80a.

In practice, the adapters 80, 80a preferably are of metal or a rigid plastic material, or a composite thereof. The bore 42 is typically about 12 mm in diameter. The outer diameters of both adapters 80, 80a is substantially 12 mm, such that adapters 80, 80a provide an interference (i.e., a close sliding) fit with bore 42. Adapter 80 is provided with an inside diameter of about 6 mm, which equates substantially to the outside diameter of guidewire sleeve 48. Adapter 80a is provided with an inside diameter of from about 6 mm to near 12 mm, equating substantially to the outside diameter of a selected drill bit, ranging in size from about 6 mm to about 12 mm.

It will be apparent that adapter 80 may be structurally similar to adapter 80a, that is, without slots 86, but provided with one or more openings therein through which thumbscrew 46 may extend to engage guidewire sleeve 48 so as to lock guidewire sleeve 48 in place (not shown). Such an embodiment requires an index means to insure alignment of the screw and one or more openings.

Figure 20:
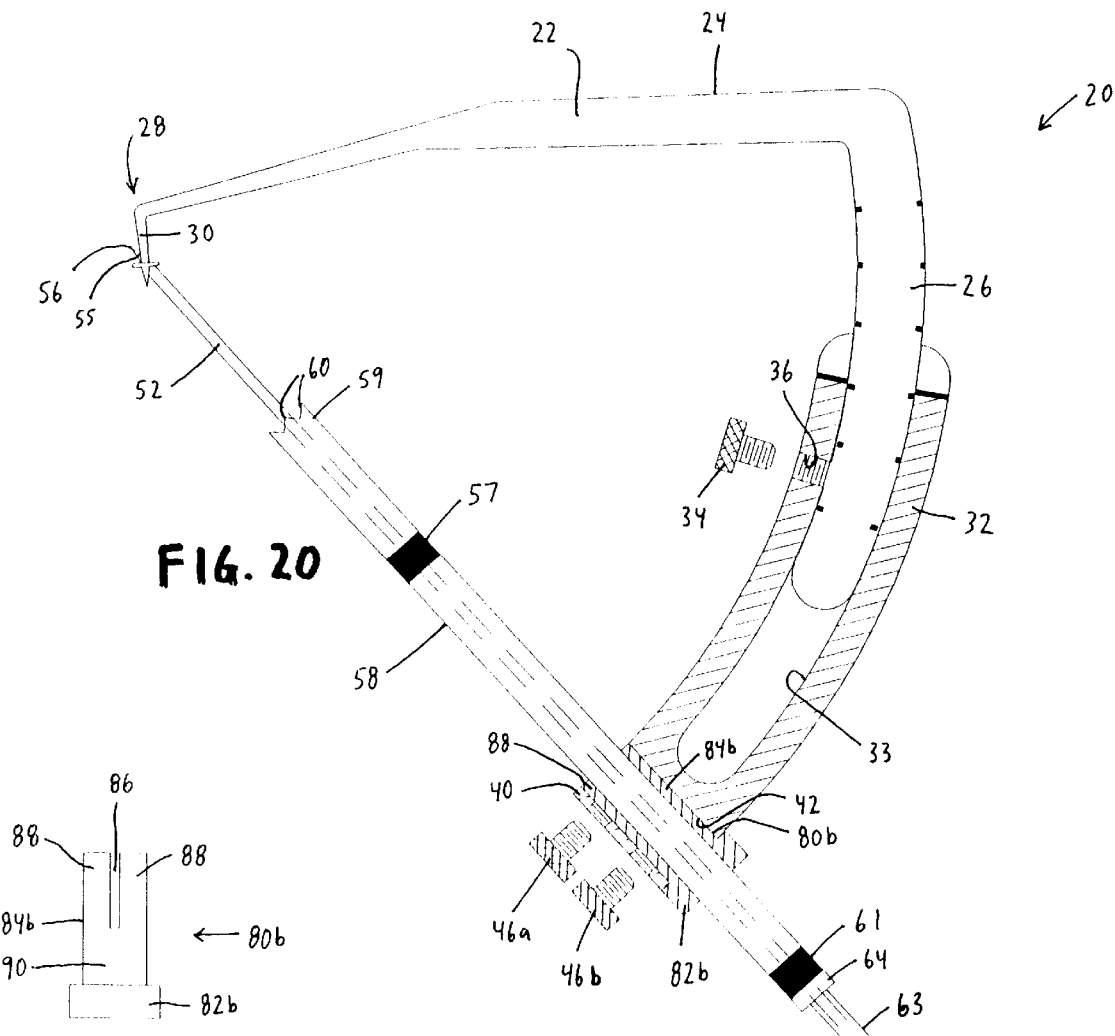
FIG. 20 is a side elevational view, partly in section, of a drill guide assembly illustrative of another alternative embodiment of the invention.

In FIG. 20 there is shown another alternative embodiment in which the assembly includes a single adapter 80b which serves to receive and retain a single tool, drill bit 58. In this embodiment, drill bit 58 serves first as a guidewire sleeve and secondly as a drill bit.

Figure 21:
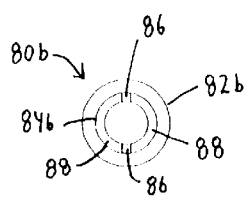
FIG. 21 is a side elevational view of a third adapter for use in the assembly of FIG. 20.

Referring to FIGS. 21 and 22, it will be seen that adapter 80b includes a head portion 82b at a first end thereof, and a body portion 84b extending from head portion 82b, the body portion 84b comprising a cylindrically-shaped tube having a plurality of slots 86 therein extending from a second end of the body portion 84b to a point removed from either end of the adapter body portion, forming fingers 88 upstanding from a base portion 90 of the adapter.

In operation of the embodiment of FIG. 20, adapter 80b is inserted into bore 42 and thumbscrew 46b is tightened to lock adapter 80b in bore 42, the inner end of screw 46b bearing against adapter base portion 90. The rack is then set in place with the probe 30 in contact with the tibia 53, and first and second guide members 22, 32 are locked together by thumbscrew 34. The rack may be pulled proximally by the operator to set the pointed tip of probe 30 in the tibia. The two collars 57, 61 are inserted into drill bit 58 and the drill bit 58 is inserted in the adapter 80b, and is moved into engagement with the tibia. The first and second guide members 22, 32 may be reset, if desired, by manipulation of thumbscrew 34. Thumbscrew 46a is then tightened to prevent drill bit 58 from moving in bore 42. Tightening of thumbscrew 46a flexes one or more fingers 88 inwardly against the drill bit to prevent movement thereof in bore 42. Guidewire 52 is then pushed through collars 61, 57 to extend just beyond toothed end 59 of drill bit 58. The guidewire 52 is then drilled through the tibia, to pass through probe orifice 38. As this occurs, collars 61, 57 (which are contained within the immobilized drill bit 58) stabilize the guidewire. Upon completion of the guidewire boring operation, the thumbscrew 46a is loosened, to permit drill bit 58 to move in adapter 80b, which is held in place by thumbscrew 46b. Drill bit 58 is then driven forward by a drill (not shown), causing the drill bit to enter the tibia and cut a tunnel therethrough.

The adapter body portion 84b may be provided with openings other than slots 86, which openings (not shown) permit passage of thumbscrew 46a therethrough to directly engage drill bit 58 and prevent the drill bit from moving in bore 42. In such case, an index means is required, such as markings on the adapter head portion 82b, to provide an indication as to the alignment of screw 46a and such openings.

It is to be understood that the present invention is by no means limited to the particular constructions and method steps herein disclosed and/or shown in the drawings, but also comprises any modifications or equivalents within the scope of the claims. For example, though for illustrative purposes, the inventive devices and methods are described hereinabove with reference to formation of a tibial tunnel, it will be appreciated by those skilled in the art that the devices and methods described herein find utility with respect to other bones, as in shoulder joints, and the like.

What is claimed is:

1. A drill guide assembly for producing a tunnel in a bone, said assembly comprising:

an adjustable rack having a probe portion for engagement with a desired bony landmark, and a tool holder portion for holding tool means for penetrating the bone;

said probe portion having an orifice therethrough; and said tool holder portion being adapted to retain said tool means such that an extension of an axis of said tool means passes through said orifice.

2. A drill guide assembly for producing a tunnel in a bone, said assembly comprising:

a rack having a probe portion for engagement with a desired bony landmark, and a tool holder portion for holding tool means for penetrating the bone;

said probe portion having an orifice therethrough; and said tool holder portion being adapted to retain said tool means such that an extension of an axis of said tool means passes through said orifice;

wherein said rack comprises:

a first guide member having said probe portion thereon and having an arm portion defining a circle about said orifice in said probe portion;

a second guide member slidably disposed on said first guide member, of a curved configuration, and disposed in the circle defined by said arm portion of said first guide member, said second guide member having said tool holder portion thereon; and locking means for securing together said first and second guide members in a selected relationship and for securing said tool means to said tool holder portion of said second guide member.

3. A drill guide assembly for producing a tunnel in a bone, said assembly comprising a rack having:

a first guide member having a first arm portion, and a second arm portion extending from said first arm portion and generally perpendicular to said first arm portion, said second arm portion being curved, said first arm portion having at a free end thereof a probe for engagement with a desired bony landmark, said probe having an orifice therethrough, said second arm portion defining a circle about said orifice;

a second guide member slidably disposed on said second arm portion of said first guide member, said second guide member being curved and disposed in the circle defined by said second arm portion, said second guide member having a bore therethrough proximate a free end thereof, the axis of said bore in said second guide member extending through said orifice in said probe; and locking means for securing together said first guide member and said second guide member in a selected relationship, and for securing bone boring means in said second guide member bore.

4. The assembly in accordance with claim 3 further comprising said bone boring means, wherein said bone boring means comprises a guidewire sleeve receivable in said bore of said second guide member, said guidewire sleeve having an axial passageway therethrough, said passageway being aligned with said orifice in said probe, and said locking means being adapted to secure said guidewire sleeve in said bore of said second guide member.

5. The assembly in accordance with claim 4 wherein said bone boring means further comprise a guidewire receivable in said guidewire sleeve passageway and adapted to be moved through said guidewire sleeve passageway, through the bone and through said orifice in said probe.

6. The assembly in accordance with claim 5 further comprising a first collar for disposition around said guidewire between said guidewire sleeve and the bone, said first collar being adapted to support said guidewire adjacent the bone.

7. The assembly in accordance with claim 6 wherein said bone boring means further comprise a drill bit receivable in said bore of said second guide member and adapted to have said guidewire extending therethrough.

8. The assembly in accordance with claim 7 wherein said drill bit comprises a coring drill bit having drilling teeth at a first end thereof and having a second collar therein adapted to have said guidewire extend therethrough.

9. The assembly in accordance with claim 8 wherein said second collar is disposed in said coring drill bit proximate a second end of said drill bit.

10. The assembly in accordance with claim 9 wherein said first and second collars are made of a material selected from a group of materials having low coefficients of friction and consisting of metal, rigid plastic, and composites thereof.

11. The assembly in accordance with claim 8 wherein said drill bit is adapted to receive said first collar through said first end of said drill bit.

12. The assembly in accordance with claim 11 wherein said first collar is movable in said drill bit by a bone core entering said drill bit as said drill bit drills into the bone.

13. The assembly in accordance with claim 12 further comprising a cylinder having an open first end for discharge of said bone core from said cylinder, and an open second end for receiving said drill bit with said bone core and said collars therein, and a plunger insertable into said drill bit and engageable with one of said collars to move said collars in said drill bit so as to push said bone core out said first end of said drill bit and into an otherwise unoccupied portion of said cylinder.

14. The assembly in accordance with claim 6 wherein said first collar is made of material selected from a group of materials having low coefficients of friction and consisting of metal, rigid plastic, and composites thereof.

15. The assembly in accordance with claim 3 further comprising adapter means for disposition in said bore, said bone boring means being receivable by said adapter means.

16. The assembly in accordance with claim 15 wherein said bone boring means comprises (1) a guidewire and guidewire sleeve, and (2) a drill bit, and said adapter means comprises (1) a first adapter for receiving and retaining said guidewire sleeve and (2) a second adapter for receiving and retaining said drill bit.

17. The assembly in accordance with claim 16 wherein said first adapter comprises a unitary member having a head portion and a body portion, said body portion comprising a cylindrically-shaped tube upstanding from said head portion and having lengthwise slots therein dividing said body portion into a plurality of fingers.

18. The assembly in accordance with claim 17 wherein said locking means comprises screw means for bearing against at least one of said fingers to press said at least one of said fingers against said guidewire sleeve to lock said sleeve in said bore.

19. The assembly in accordance with claim 18 wherein said second adapter comprises a unitary member having a head portion and a body portion, said body portion comprising a cylindrically-shaped tube upstanding from said head portion.

20. The assembly in accordance with claim 19 wherein said locking means comprises screw means for bearing against said body portion to lock said second adapter in said bore.

21. The assembly in accordance with claim 15 wherein said bone boring means comprises a coring drill bit receivable by said adapter means and a guidewire receivable by said drill bit, and said locking means for securing bone boring means in said second guide member comprises screw means for locking said adapter means in said bore and for locking said drill bit in said adapter.

22. The assembly in accordance with claim 21 wherein said adapter means comprises a unitary adapter member having a base portion adapted to receive a first portion of said screw means for locking said adapter in said bore, and a body portion adapted to receive a second portion of said screw means for locking said drill bit in said adapter, such that said drill bit is prevented from moving in said bore, but said guidewire is free to move in said drill bit.

23. The assembly in accordance with claim 22 wherein said base portion of said adapter comprises a cylindrically-shaped tube and said body portion comprises a plurality of fingers upstanding from said base portion, said second portion of said screw means being adapted to press one of said fingers against said drill bit to lock said drill bit in said adapter.

24. A drill guide assembly for producing a tunnel in a bone and preserving a bone core resulting from the tunnel production, said assembly comprising:
   a rack having a probe portion for engagement with a desired bony landmark, tool means and a tool holder portion for holding said tool means for penetrating the bone;
   said tool means including a coring drill bit adapted for mounting in said tool holder portion of said rack, said drill bit having teeth at a first end thereof;
   said first end of said drill bit being adapted to receive a first collar mounted between said first end of said drill bit and the bone on a guidewire extending through said drill bit and the bone;
   said drill bit being adapted to permit sliding movement of said first collar in said drill bit as said drill bit enters the bone and a drilled-out core portion of the bone extends progressively into said drill bit.

25. A drill guide assembly for producing a tunnel in a bone and preserving a bone core resulting from the tunnel production, said assembly comprising:
   a rack having a probe portion for engagement with a desired bony landmark, tool means and a tool holder portion for holding said tool means for penetrating the bone;
   said tool means including a coring drill bit adapted for mounting in said tool holder portion of said rack, said drill bit having teeth at a first end thereof;
   said first end of said drill bit being adapted to receive a first collar mounted between said first end of said drill bit and the bone on a guidewire extending through said drill bit and the bone;
   said drill bit being adapted to permit sliding movement of said first collar in said drill bit as said drill bit enters the bone and a drilled-out core portion of the bone extends progressively into said drill bit;
   said drill bit being adapted to receive a second collar disposed in said drill bit proximate a second end of said drill bit and adapted to have said guidewire extend therethrough.

26. The assembly in accordance with claim 25 further comprising a plunger for insertion into said drill bit through an opening in said second end of said drill bit, said plunger being engageable with said second collar for pushing said second collar, said first collar, and the bone core toward said first end of said drill bit for expelling the bone core from said first end of said drill bit.

27. A drill guide assembly for producing a tunnel in a bone and preserving a bone core resulting from the tunnel production, said assembly comprising:
   a rack having a probe portion for engagement with a desired bony landmark, tool means and a tool holder portion for holding said tool means for penetrating the bone;
   said tool means including a coring drill bit adapted for mounting in said tool holder portion of said rack, said drill bit having teeth at a first end thereof;
   said first end of said drill bit being adapted to receive a first collar mounted between said first end of said drill bit and the bone on a guidewire extending through said drill bit and the bone;
   said drill bit being adapted to permit sliding movement of said first collar in said drill bit as said drill bit enters the bone and a drilled-out core portion of the bone extends progressively into said drill bit;
   further comprising a plunger for insertion into said drill bit through an opening in said second end of said drill bit for pushing said first collar toward said first end of said drill bit so as to move said drilled-out core portion out of said drill bit through said first end of said drill bit.

28. A drill guide assembly for producing a tunnel in a bone and preserving a bone core resulting from the tunnel production, said assembly comprising:
   a rack including a first guide member having a first arm portion, and a second arm portion extending from said first arm portion and generally perpendicular to said first arm portion, said second arm portion being curved, said first arm portion having at a free end thereof a probe for engagement with a desired bony landmark, said second arm portion defining a circle about said probe, a second guide member slidably disposed on said second arm portion of said first guide member, said second guide member being curved and disposed in the circle defined by said second arm portion, said second guide member having a bore therethrough proximate a free end thereof, an extension of the axis of said bore in said second guide member extending through said probe, and first locking means for securing together said first guide member and said second guide member in a selected relationship; and
   coring drill means adapted for insertion into said bore of said second guide member, said coring drill means comprising a cylindrically-shaped drill bit having teeth at a first end thereof, said first end of said drill bit being adapted to receive a first collar mounted between said drill bit and the bone on a guidewire extending through said drill bit and the bone, said drill bit being adapted to permit sliding movement of said first collar in said drill bit as said drill bit enters the bone and a drilled-out core portion of the bone extends progressively into said drill bit.

29. The assembly in accordance with claim 17 wherein said first collar is made of a material elected from a group of materials having low coefficients of friction and consisting of metal, rigid plastic, and composites thereof.

30. A drill guide assembly for producing a tunnel in a bone and preserving a bone core resulting from the tunnel production, said assembly comprising:
   a rack including a first guide member having a first arm portion, and a second arm portion extending from said first arm portion and generally perpendicular to said first arm portion, said second arm portion being curved, said first arm portion having at a free end thereof a probe for engagement with a desired bony landmark, said second arm portion defining a circle about said probe, a second guide member slidably disposed on said second arm portion of said first guide member, said second guide member being curved and disposed in the circle defined by said second arm portion, said second guide member having a bore therethrough proximate a free end thereof, an extension of the axis of said bore in said second guide member extending through said probe, and first locking means for securing together said first guide member and said second guide member in a selected relationship; and coring drill means adapted for insertion into said bore of said second guide member, said coring drill means comprising a cylindrically-shaped drill bit having teeth at a first end thereof, said first end of said drill bit being adapted to receive a first collar mounted between said drill bit and the bone on a guidewire extending through said drill bit and the bone, said drill bit being adapted to permit sliding movement of said first collar in said drill bit as said drill bit enters the bone and a drilled-out core portion of the bone extends progressively into said drill bit;

said drill bit being adapted to receive a second collar disposed in said drill bit proximate a second end thereof, and adapted to have said guidewire extend therethrough.

31. The assembly in accordance with claim 30 further comprising a plunger for insertion into said drill bit through an opening in said second end of said drill bit, said plunger being engageable with said second collar for pushing said second collar, said first collar, and the bone core toward said first end of said drill bit for expelling the core from said first end of said drill bit.

32. The assembly in accordance with claim 31 further comprising a cylinder having open first and second ends, said second end of said cylinder being adapted to receive said drill bit therein and retain said drill bit therein with said first end of said drill bit removed from said first end of said cylinder, whereby said movement of the bone core out of said drill bit causes the bone core to enter an otherwise unoccupied portion of said cylinder adjacent said first end of said cylinder and to be loosely retained by said cylinder until removal of the bone core from said cylinder through said first end of said cylinder.

33. The assembly in accordance with claim 30 wherein said first and second collars are made of a material selected from a group of materials having low coefficients of friction and consisting of metal, rigid plastic, and composites thereof.

34. A drill guide assembly for producing a tunnel in a bone and preserving a bone core resulting from the tunnel production, said assembly comprising:

a rack including a first guide member having a first arm portion, and a second arm portion extending from said first arm portion and generally perpendicular to said first arm portion, said second arm portion being curved, said first arm portion having at a free end thereof a probe for engagement with a desired bony landmark, said second arm portion defining a circle about said probe, a second guide member slidably disposed on said second arm portion of said first guide member, said second guide member being curved and disposed in the circle defined by said second arm portion, said second guide member having a bore therethrough proximate a free end thereof, an extension of the axis of said bore in said second guide member extending through said probe, and first locking means for securing together said first guide member and said second guide member in a selected relationship; and coring drill means adapted for insertion into said bore of said second guide member, said coring drill means comprising a cylindrically-shaped drill bit having teeth at a first end thereof, said first end of said drill bit being adapted to receive a first collar mounted between said drill bit and the bone on a guidewire extending through said drill bit and the bone, said drill bit being adapted to permit sliding movement of said first collar in said drill bit as said drill bit enters the bone and a drilled-out core portion of the bone extends progressively into said drill bit;

further comprising a plunger for insertion into said drill bit through an opening in said second end of said drill bit for pushing said first collar toward said first end of said drill bit to move the bone core out of said drill bit through said first end of said drill bit.

35. The assembly in accordance with claim 34 further comprising a cylinder having open first and second ends, said second end of said cylinder being adapted to receive said drill bit therein and retain said drill bit therein with said first end of said drill bit removed from said first end of said cylinder, whereby said movement of the bone core out of said drill bit causes the bone core to enter an otherwise unoccupied portion of said cylinder adjacent said first end of said cylinder and to be loosely retained by said cylinder until removal of the bone core from said cylinder through said first end of said cylinder.

36. A method for producing a tunnel in a bone, the method comprising the steps of:

providing a drill guide assembly comprising a rack having a probe portion for engagement with a desired bony landmark, and a tool holder portion for holding tool means for penetrating the bone, said probe portion having an orifice therein, said tool holder portion being adapted to hold said tool means with an extension of the axis of said tool means passing through said orifice, said tool means comprising a guidewire sleeve for connection to said tool holder portion of said rack, said tool means further comprising a coring drill bit adapted for connection to said tool holder portion of said rack, a guidewire for extending axially through said guidewire sleeve and said drill bit, respectively, and collar means for mounting on said guidewire;

fixing said guidewire sleeve to said tool holder portion of said rack;

sliding said guidewire through said guidewire sleeve;

sliding said collar means onto said guidewire at a distal end of said guidewire;

engaging a desired bony landmark on the surface of the bone with said probe portion;

moving said distal end of said guidewire and said collar means into engagement with the bone; extending said guidewire through the bone and through said orifice in said probe portion of said rack;

removing said guidewire sleeve from said tool holder portion of said rack;

attaching said coring drill bit to said tool holder portion of said rack, with said guidewire extending through said drill bit and a cutting end of said drill bit adjacent to said collar means which is adjacent to the bone; and advancing said drill bit into the bone, with said collar means being forced into said drill bit, and progressively further into said drill bit as said drill bit advances into the bone and a bone core cut by said drill bit enters said drill bit;

whereby to produce the tunnel in the bone and capture the bone core produced thereby.

37. The method in accordance with claim 36 wherein after moving said guidewire and said collar means into engagement with the bone, said guidewire sleeve is loosened, moved into engagement with said collar means and tightened in place, prior to extending said guidewire through the bone.

38. The method in accordance with claim 36 comprising the further steps of:

detaching said drill bit from said tool holder portion of said rack and from said guidewire;

providing a plunger insertable into a second end of said drill bit; and inserting said plunger into said drill bit through said second end of said drill bit to push said collar means toward said cutting end of said drill bit to move said bone core out of said drill bit.

39. The method in accordance with claim 38 comprising the further steps of:

providing a cylinder having first and second open ends, said second end being adapted to receive and retain said drill bit; and placing said drill bit in said cylinder, with said second end of said drill bit proximate to and retained by said second end of said cylinder;

whereby upon moving of said bone core out of said drill bit, said core enters a portion of said cylinder not occupied by said drill bit and in which said core is confined.

40. A method for producing a tunnel in a bone, the method comprising the steps of:

providing a drill guide assembly comprising a rack having a probe portion for engagement with a desired bony landmark and a tool holder portion for holding tool means for penetrating the bone, said probe portion having an orifice therein, said tool holder portion being adapted to hold said tool means with an extension of the axis of said tool means passing through said orifice, said tool means comprising a guidewire sleeve for connection to said tool holder portion of said rack, a guidewire for extending axially through said guidewire sleeve, and collar means for mounting on said guidewire;

engaging a desired bony landmark on the surface of the bone with said probe portion;

fixing said guidewire sleeve to said tool holder portion of said rack;

moving said distal end of said guidewire sleeve into engagement with the bone;

sliding said guidewire through said guidewire sleeve;

extending said guidewire through the bone and through said orifice in said probe portion of said rack;

removing said guidewire sleeve from said tool holder portion of said rack;

sliding said collar means onto said guidewire from a proximal end of said guidewire and positioning said collar means proximate the bone;

attaching a coring drill bit to said tool holder portion of said rack, with said guidewire extending through said drill bit and a cutting end of said drill bit adjacent to said collar means which is proximate the bone; and advancing said drill bit into the bone, with said collar means being forced into said drill bit, and progressively further into said drill bit as said drill bit advances into the bone, and a bone core cut by said drill bit enters said drill bit;

whereby to produce the tunnel in the bone and capture the bone core produced thereby.

41. The method in accordance with claim 40 comprising the further steps of:

detaching said drill bit from said tool holder portion of said rack and from said guidewire;

providing a plunger insertable into a second end of said drill bit; and inserting said plunger into said drill bit through said second end of said drill bit to push said collar means toward said cutting end of said drill bit to move said bone core out of said drill bit.

42. The method in accordance with claim 41 comprising the further steps of:

providing a cylinder having first and second open ends, said second end being adapted to receive and retain said drill bit; and placing said drill bit in said cylinder, with said second end of said drill bit proximate to and retained by said second end of said cylinder;

whereby upon moving of said bone core out of said drill bit, said core enters a portion of said cylinder not occupied by said drill bit and in which said core is confined.

43. A method for producing a tunnel in a bone, the method comprising the steps of:

providing a drill guide assembly comprising a rack having a probe portion for engagement with a desired bony landmark and a tool holder portion for holding tool means for penetrating the bone, said probe portion having an orifice therein, said tool holder portion being adapted to hold said tool means with an extension of the axis of said tool means passing through said orifice, said tool means comprising a coring drill bit for connection to said tool holder portion of said rack, said tool means further comprising a guidewire adapted to extend axially through said drill bit, and collar means for mounting in said drill bit and in which is mountable said guidewire;

engaging a desired bony landmark on the surface of the bone with said probe portion;

connecting said coring drill bit, with said collar means therein, to said tool holder portion;

moving said coring drill bit into engagement with the bone;

locking said coring drill bit to said tool holder to prevent movement of said drill bit in said tool holder;

passing said guidewire through said collar means in said drill bit;

drilling said guidewire through the bone, passing a distal end of said guidewire through said probe orifice;

unlocking said coring drill bit to permit movement of said drill bit in said tool holder; and rotating and advancing said coring drill bit to cut the tunnel through the bone, whereby to produce the tunnel in the bone and capture the bone core produced thereby.

44. The method in accordance with claim 43 comprising the further steps of:

detaching said drill bit from said tool holder portion of said rack and from said guidewire;

providing a plunger insertable into a second end of said drill bit; and inserting said plunger into said drill bit through said second end of said drill bit to push said collar means toward said cutting end of said drill bit to move said bone core out of said drill bit.

45. The method in accordance with claim 44 comprising the further steps of:

providing a cylinder having first and second open ends, said second end being adapted to receive and retain said drill bit; and placing said drill bit in said cylinder, with said second end of said drill bit proximate to and retained by said second end of said cylinder;

whereby upon moving of said bone core out of said drill bit, said core enters a portion of said cylinder not occupied by said drill bit and in which said core is confined.

* * * * *